US011076887B2

(12) United States Patent
Yacoub et al.

(10) Patent No.: US 11,076,887 B2
(45) Date of Patent: Aug. 3, 2021

(54) ORTHOPEDIC FIXATION DEVICES AND METHODS OF INSTALLATION THEREOF

(71) Applicant: GLOBUS MEDICAL, INC., Audubon, PA (US)

(72) Inventors: George Yacoub, Egg Harbor Township, NJ (US); Jeff Nichols, Philadelphia, PA (US)

(73) Assignee: Globus Medical, Inc., Audubon, PA (US)

( * ) Notice: Subject to any disclaimer, the term of this patent is extended or adjusted under 35 U.S.C. 154(b) by 48 days.

(21) Appl. No.: 15/982,587

(22) Filed: May 17, 2018

(65) Prior Publication Data

US 2018/0263665 A1 Sep. 20, 2018

Related U.S. Application Data

(60) Continuation-in-part of application No. 14/849,736, filed on Sep. 10, 2015, now Pat. No. 9,993,269, which is a continuation-in-part of application No. 14/514,796, filed on Oct. 15, 2014, now Pat. No. 9,549,763, which is a division of application No. 13/183,965, filed on Jul. 15, 2011, now Pat. No. 8,888,827.

(51) Int. Cl.
*A61B 17/70* (2006.01)
*A61B 17/88* (2006.01)
*A61B 17/86* (2006.01)

(52) U.S. Cl.
CPC ...... *A61B 17/7035* (2013.01); *A61B 17/7032* (2013.01); *A61B 17/7037* (2013.01); *A61B 17/7056* (2013.01); *A61B 17/7082* (2013.01); *A61B 17/8605* (2013.01); *A61B 17/8615* (2013.01); *A61B 17/888* (2013.01)

(58) Field of Classification Search
CPC ............ A61B 17/7035; A61B 17/7032; A61B 17/7056; A61B 17/7082
USPC .......................................................... 606/273
See application file for complete search history.

(56) References Cited

U.S. PATENT DOCUMENTS

| | | |
|---|---|---|
| 5,716,356 A | 2/1998 | Biedermann et al. |
| 6,485,491 B1 | 11/2002 | Farris et al. |
| 6,695,846 B2 | 2/2004 | Richelsoph et al. |
| 7,678,136 B2 | 3/2010 | Doubler et al. |
| 8,016,866 B2 * | 9/2011 | Warnick ............. A61B 17/7032 606/305 |
| 8,221,457 B2 | 7/2012 | Delecrin et al. |
| 8,435,266 B2 | 5/2013 | Richelsoph |
| 8,657,857 B2 | 2/2014 | Dall et al. |
| 9,055,980 B2 | 6/2015 | Biedermann |

(Continued)

FOREIGN PATENT DOCUMENTS

| | | |
|---|---|---|
| DE | 9314297 U1 | 5/1994 |
| EP | 1459690 A1 | 9/2004 |

(Continued)

*Primary Examiner* — Matthew J Lawson

(57) ABSTRACT

Orthopedic fixation devices and methods of installing the same. The orthopedic fixation device may include a coupling element and a bone fastener, whereby the bone fastener can be loaded into the coupling element through the bottom of a bore in the coupling element. A retaining clip disposed below the fastener in an annular channel of the coupling element has an inner diameter which is less than a maximum diameter of the head of the bone fastener.

18 Claims, 26 Drawing Sheets

(56) References Cited

U.S. PATENT DOCUMENTS

| | | |
|---|---|---|
| 9,060,814 B2 * | 6/2015 | Doubler .............. A61B 17/704 |
| 9,333,016 B2 * | 5/2016 | Biedermann ........ A61B 17/844 |
| 9,615,867 B2 | 4/2017 | Picetti et al. |
| 9,820,780 B2 | 11/2017 | Duncan et al. |
| 2002/0035366 A1 | 3/2002 | Walder et al. |
| 2004/0116929 A1 * | 6/2004 | Barker .............. A61B 17/7037 606/266 |
| 2004/0267264 A1 | 12/2004 | Konieczynski et al. |
| 2005/0131410 A1 * | 6/2005 | Lin .................. A61B 17/7032 606/266 |
| 2005/0171537 A1 | 8/2005 | Mazel et al. |
| 2005/0187548 A1 * | 8/2005 | Butler .............. A61B 17/7032 606/278 |
| 2005/0228385 A1 | 10/2005 | Iott et al. |
| 2005/0283157 A1 * | 12/2005 | Coates .............. A61B 17/7037 606/268 |
| 2006/0079892 A1 | 4/2006 | Roychowdhury et al. |
| 2006/0161152 A1 * | 7/2006 | Ensign .............. A61B 17/7032 606/278 |
| 2006/0200128 A1 * | 9/2006 | Mueller ............ A61B 17/7032 606/308 |
| 2006/0217716 A1 * | 9/2006 | Baker .............. A61B 17/7032 606/308 |
| 2006/0241599 A1 * | 10/2006 | Konieczynski .... A61B 17/7032 606/278 |
| 2006/0241603 A1 * | 10/2006 | Jackson .............. A61B 17/8605 606/304 |
| 2007/0088357 A1 * | 4/2007 | Johnson ............ A61B 17/7032 606/86 A |
| 2007/0118117 A1 * | 5/2007 | Altarac ............ A61B 17/7037 606/270 |
| 2007/0233080 A1 * | 10/2007 | Na .................. A61B 17/7032 606/278 |
| 2008/0045955 A1 * | 2/2008 | Berrevoets ........ A61B 17/7032 606/272 |
| 2008/0114362 A1 | 5/2008 | Justis et al. |
| 2008/0243185 A1 * | 10/2008 | Felix .................. A61B 17/7032 606/246 |
| 2008/0249576 A1 * | 10/2008 | Hawkes ............ A61B 17/7037 606/305 |
| 2008/0294202 A1 | 11/2008 | Peterson et al. |
| 2009/0030457 A1 * | 1/2009 | Janowski .......... A61B 17/7032 606/246 |
| 2009/0036929 A1 * | 2/2009 | Reglos .............. A61B 17/7035 606/278 |
| 2009/0082819 A1 * | 3/2009 | Blain ................ A61B 17/7032 606/308 |
| 2010/0063552 A1 * | 3/2010 | Chin ................ A61B 17/7032 606/302 |
| 2010/0152787 A1 | 6/2010 | Walsh et al. |
| 2011/0040335 A1 | 2/2011 | Stihl et al. |
| 2011/0077694 A1 * | 3/2011 | Biedermann ...... A61B 17/7032 606/305 |
| 2011/0106173 A1 | 5/2011 | Lindemann et al. |
| 2011/0160779 A1 | 6/2011 | Schlaepfer et al. |
| 2012/0071926 A1 | 3/2012 | Jani et al. |
| 2012/0116462 A1 * | 5/2012 | Arambula .......... A61B 17/7037 606/305 |
| 2013/0274806 A1 * | 10/2013 | Jackson ............ A61B 17/7032 606/272 |
| 2015/0223844 A1 | 8/2015 | Leff et al. |
| 2015/0359568 A1 | 12/2015 | Rezach |
| 2016/0302831 A1 | 10/2016 | Nichols et al. |
| 2017/0095271 A1 | 4/2017 | Faulhaber |
| 2017/0311985 A1 | 11/2017 | Bobbitt et al. |
| 2018/0014863 A1 | 1/2018 | Biester et al. |

FOREIGN PATENT DOCUMENTS

| | | |
|---|---|---|
| FR | 2720262 A1 | 12/1995 |
| WO | 2017069930 A2 | 4/2017 |

* cited by examiner

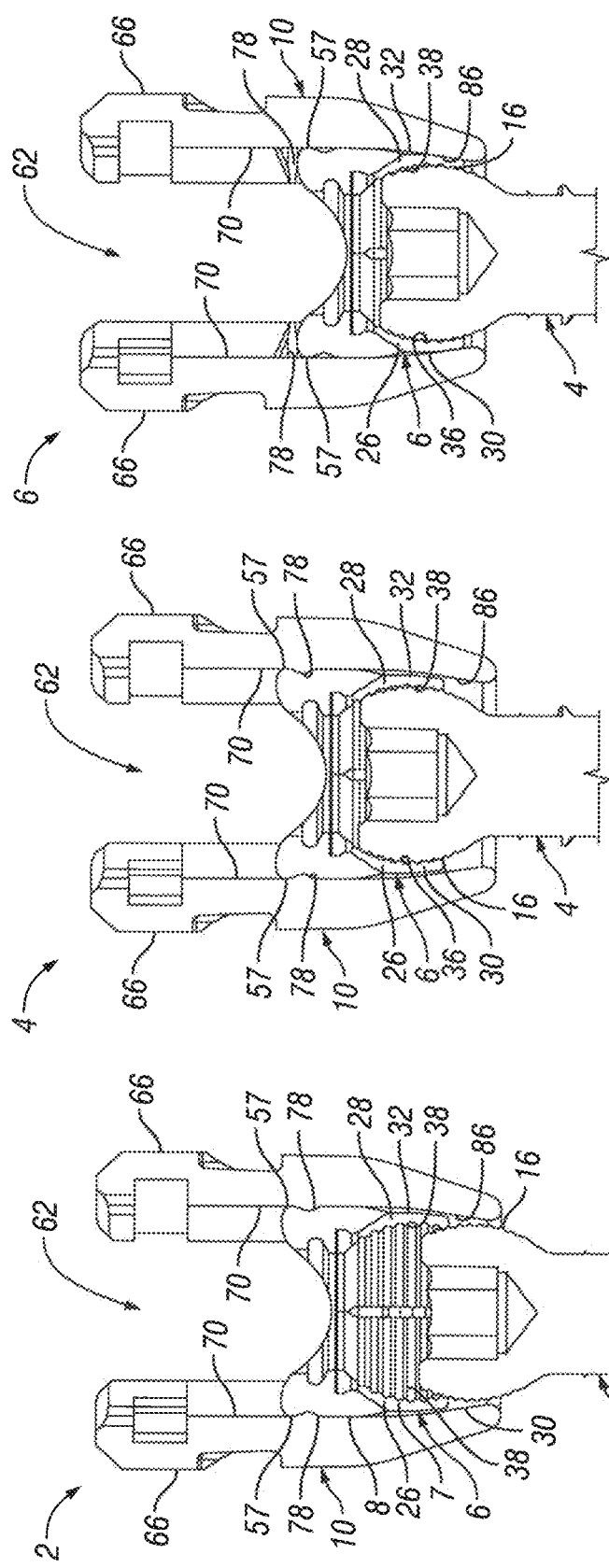

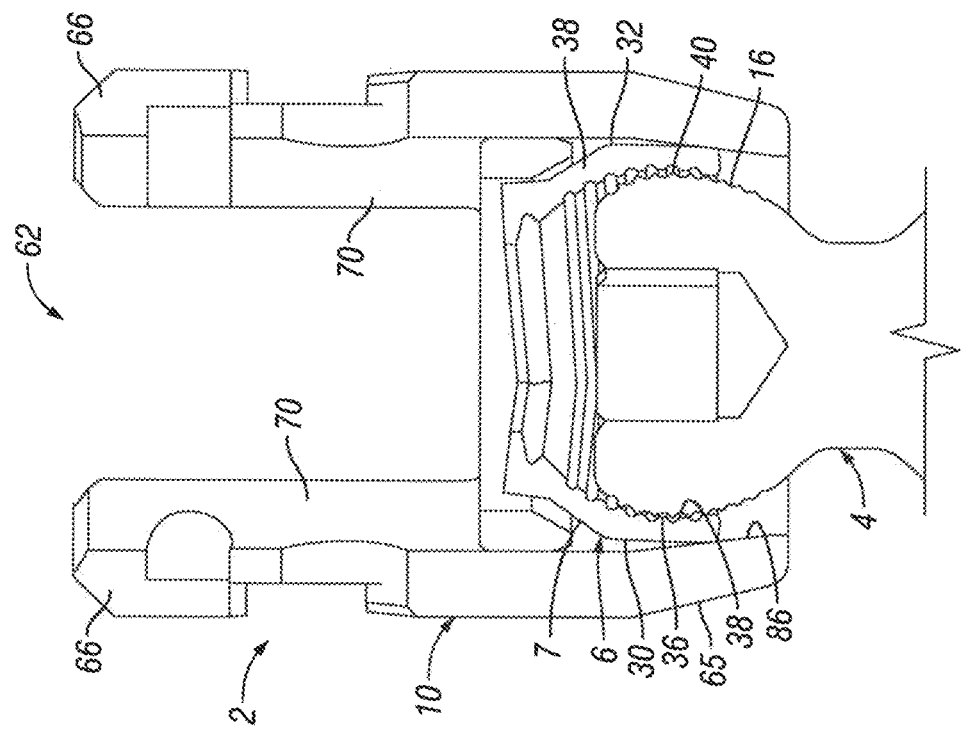
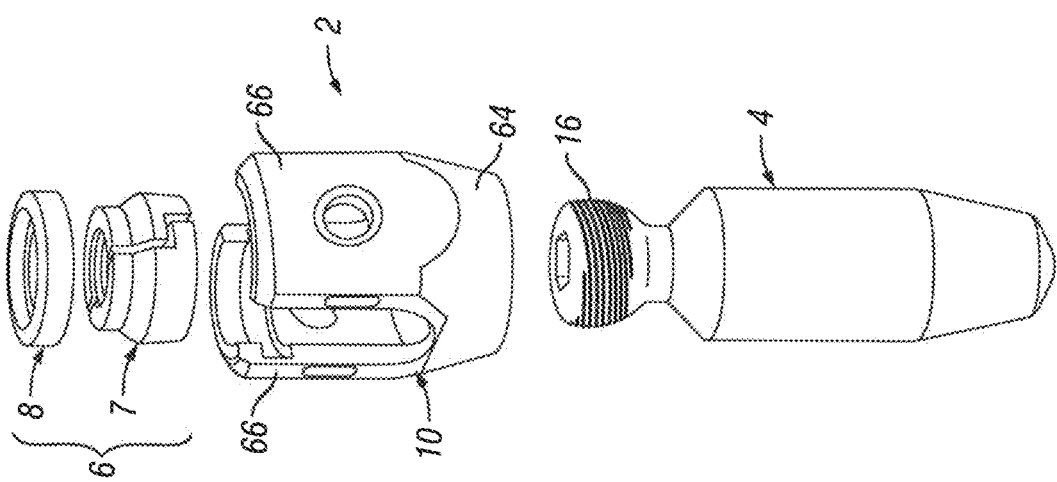
FIG. 21
FIG. 20

ORTHOPEDIC FIXATION DEVICES AND METHODS OF INSTALLATION THEREOF

CROSS REFERENCE TO RELATED APPLICATIONS

This application is a continuation-in-part of U.S. patent application Ser. No. 14/849,736, filed on Sep. 10, 2015, which is a continuation-in-part of U.S. patent application Ser. No. 14/514,796, filed on Oct. 15, 2014, now U.S. Pat. No. 9,549,763, which is a divisional of U.S. patent application Ser. No. 13/183,965, filed on Jul. 15, 2011, now U.S. Pat. No. 8,888,827, the contents of which are incorporated by reference herein in their entireties for all purposes.

FIELD OF THE INVENTION

The present invention relates to orthopedic fixation devices, and, in one or more embodiments, to an orthopedic fixation device configured for loading of the bone fastener from the bottom of the tulip element.

BACKGROUND OF THE INVENTION

Many types of spinal irregularities can cause pain, limit range of motion, or injure the nervous system within the spinal column. These irregularities can result from, without limitation, trauma, tumor, disc degeneration, and disease. Often, these irregularities are treated by immobilizing a portion of the spine. This treatment typically involves affixing a plurality of fixation devices to one or more vertebrae and connecting the devices to an elongate rod that generally extends in the direction of the axis of the spine.

Treatment for these spinal irregularities often involves using a system of fixation devices to attain stability between spinal segments. Instability in the spine can create stress and strain on neurological elements, such as the spinal cord and nerve roots. In order to correct this, implants of certain stiffness can be implanted to restore the correct alignment and portion of the vertebral bodies. In many cases, a fixation device along with a vertical solid member can help restore spinal elements to a pain free situation, or at least may help reduce pain or prevent further injury to the spine.

Typically, fixation devices may include a bone fastener (e.g., bone screw, hook, etc.) for coupling the fixation device to vertebra. Fixation devices further may include a tulip element for coupling the bone fastener to the elongated rod. Clamp and/or wedge elements may be used to secure the bone fastener in the tulip element. A locking cap may be used to secure the rod in the tulip element. While these designs can be used in the treatment of spinal irregularities, they typically require loading of the bone fastener from the top of the tulip element. One drawback to this top-loading design is that different sizes of the tulip element must be used based on the diameter of the bone fastener to accommodate passage of the fastener through the tulip element, as the inner bore of the tulip element will generally need to be larger than either the combined size of the bone fastener head and clamp element or the bone fastener diameter. Another drawback to this top-loading design is that bone hooks cannot be used as they will generally not pass through the tulip element. Yet another drawback to this top-loading design is that bone fastener must be installed in the bone while attached to the tulip element.

Accordingly, there exists a need for new and improved orthopedic fixation devices.

SUMMARY OF THE INVENTION

In an exemplary embodiment, the present invention provides an orthopedic fixation device. The orthopedic fixation device may comprise a coupling element, the coupling element may comprise a bore there through and an interior surface disposed about the bore. The orthopedic fixation device further may comprise a bone fastener, wherein the bone fastener comprises a head and an extension that extends from the head, wherein the head is configured for loading into the coupling element through the bottom of the bore. The orthopedic fixation device further may comprise a locking clamp assembly. The locking clamp assembly may comprise a clamp element, wherein the clamp element comprises a first clamp portion and a second clamp portion, wherein the first and second clamp portions each have an outer surface and an inner surface, wherein at least a portion of the outer surface is configured to engage the interior surface of the coupling element, and wherein at least a portion of the inner surface is configured to engage the head of the bone fastener. The locking clamp assembly further may comprise a wedge element, wherein the wedge element comprises a wedge bore configured to receive an upper portion of the clamp element and an inner wedge surface disposed around at least a lower portion of the wedge bore, wherein the inner wedge surface is configured to engage at least portion of the outer surface of the first and second clamp portions.

In another exemplary embodiment, the orthopedic fixation device includes a coupling element, a bone fastener, and a locking clamp assembly. The coupling element comprises a bore extending therethrough and an interior surface disposed about the bore. The bone fastener comprises a head and an extension that extends from the head, wherein the head is configured for loading into the coupling element through the bottom of the bore. The locking clamp assembly comprises a clamp element and a wedge element. The clamp element has a spherical outer surface, a spherical inner surface, and a plurality of slits extending through the clamp element, wherein at least a portion of the outer surface is configured to engage the interior surface of the coupling element, and wherein at least a portion of the inner surface is configured to engage the head of the bone fastener. The wedge element comprises a wedge bore configured to receive an upper portion of the clamp element and an inner wedge surface disposed around at least a lower portion of the wedge bore, wherein the inner wedge surface is configured to engage at least a portion of the outer surface of the clamp element. The bone fastener is configured to angulate relative to the coupling element. In addition, the clamp element may be configured to angulate relative to the coupling element. This may allow the bone fastener to be angled up to 50 degrees relative to the coupling element.

Further areas of applicability of the present invention will become apparent from the detailed description provided hereinafter. It should be understood that the detailed description and specific examples, while indicating the preferred or exemplary embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 12-14 illustrate an alternative orthopedic fixation device in accordance with embodiments of the present invention;

FIGS. 20-22 illustrate yet another alternative orthopedic fixation device in accordance with embodiments of the present invention;

DETAILED DESCRIPTION OF THE PREFERRED EMBODIMENTS

Embodiments of the present invention are generally directed to orthopedic fixation devices configured for bottom loading of the bone fastener. Instead of loading the bone fastener from the top of the tulip element, embodiments of the present invention load the bone fastener from the bottom of the tulip element. With the bone fastener loaded in the tulip element, a locking clamp assembly can then be used to secure the bone fastener therein. Thus, unlike prior orthopedic fixation devices, embodiments of the present invention permit the use of larger bone fasteners without having to also increase the size of the tulip element. This should, for example, reduce the needed inventory, decreasing the necessary graphic cases needed to perform a similar procedure, while decreasing in-house inventory costs.

Further, as explained by the examples and illustrations below, the bone fastener of the orthopedic fixation devices can be placed in the vertebra without the tulip element in accordance with embodiments of the present invention. The tulip element can then be attached to the bone fastener in situ. This should reduce the material in the surgical wound, thus increasing visualization for disc preparation and interbody procedures, for example. The bone fastener can also be used to distract or otherwise manipulate the surgical site, further increasing visualization and ease of surgery, for example. Additionally, site preparation can be performed, in some embodiments, after the bone fastener has been placed, which may allow for more accurate pedicle decortication.

Figure 1:
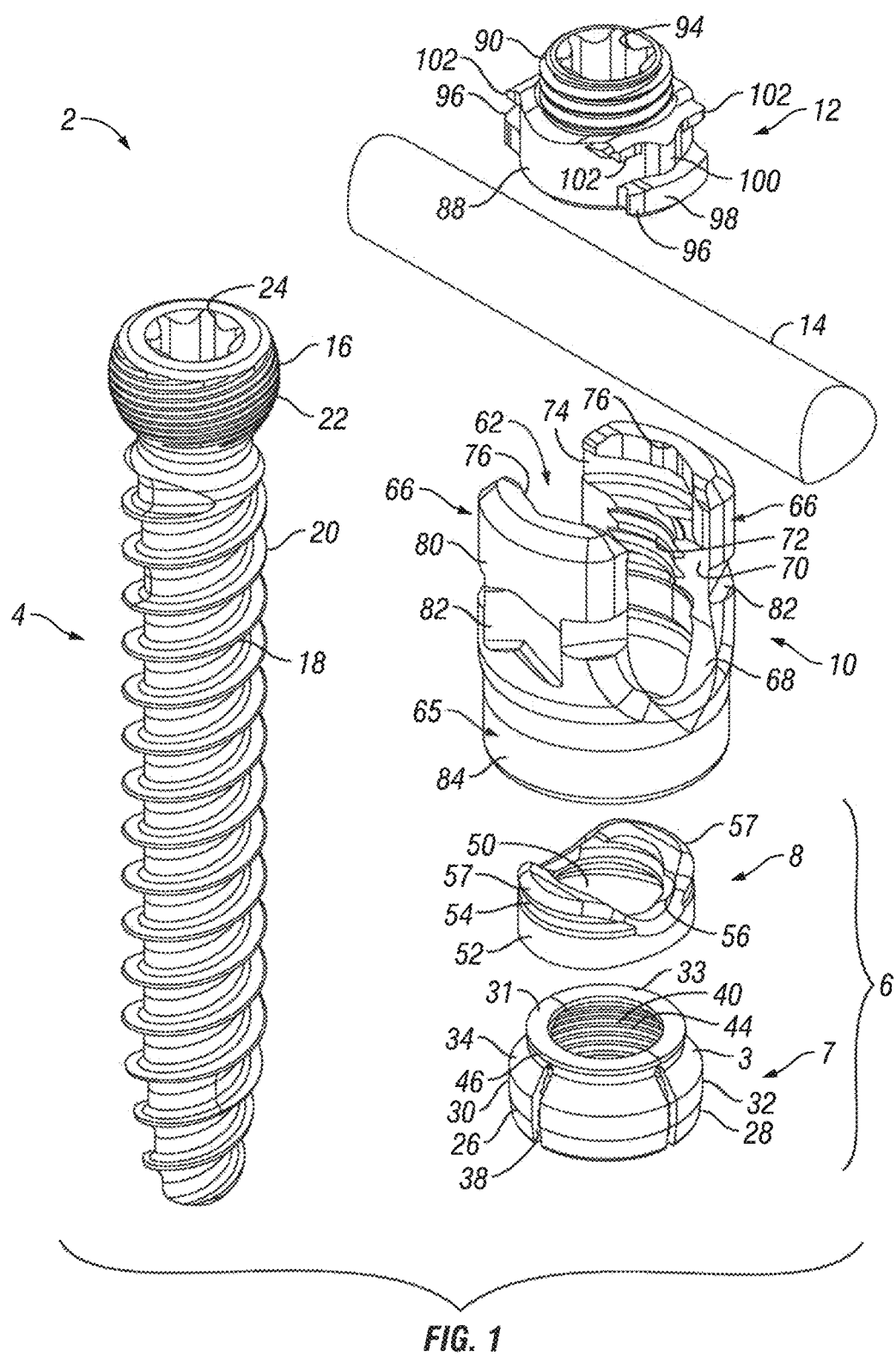
FIG. 1 is an exploded view of an orthopedic fixation device in accordance with embodiments of the present invention.

Turning now to FIG. 1, an exploded view of an orthopedic fixation device 2 is illustrated in accordance with embodiments of the present invention. As illustrated, the orthopedic fixation device 2 may comprise a bone fastener 4, a locking clamp assembly 6 (which may comprise, for example, a clamp element 7 and a wedge element 8), a tulip element 10, and a locking cap assembly 12. As will be discussed in more detail below, the bone fastener 4 may be loaded from the bottom of the tulip element 10 with the locking clamp assembly 6 already loaded therein. Prior to being locked into place, the tulip element 10 can be moved and rotated into a plurality of positions with respect to the bone fastener 4. Once the tulip element 10 is at the desired position with respect to the bone fastener 4, the tulip element 10 may be locked onto the bone fastener 4. In the illustrated embodiment, the locking cap assembly 12 is configured to secure a rod 14 in the tulip element 10. In one embodiment, the tulip element 10 is fixed onto the bone fastener 4 contemporaneously with securing of the rod 14 in the tulip element 10.

As illustrated by FIG. 1, the bone fastener 4 includes a head 16 and a shaft 18 that extends from the head 16. The illustrated embodiment shows the shaft 18 having a tapered shape and threads 20. Those of ordinary skill in the art will appreciate that the shaft 18 may have a number of different features, such as thread pitch, shaft diameter to thread diameter, overall shaft shape, and the like, depending, for example, on the particular application. While the head 16 may have any general shape, at least a portion of the head 16 may have a curved surface in order to allow for rotational movement or angular adjustment of the bone fastener 4 with respect to the tulip element 10. For example, at least a portion of the head 16 may be shaped to form a portion of a ball or at least a portion of a sphere. As illustrated, the head 16 may have a roughened or textured surface 22 that improves engagement with the clamp element 7. In certain embodiments, the head 16 may have a tool engagement surface, for example, that can be engaged by a screw-driving tool or other device. The tool engagement surface can permit the physician to apply torsional or axial forces to the bone fastener 4 to drive the bone fastener 4 into the bone. In the illustrated embodiment, the tool engagement surface of the head 16 is a polygonal recess 24. For instance, the polygonal recess 24 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

Figure 2:
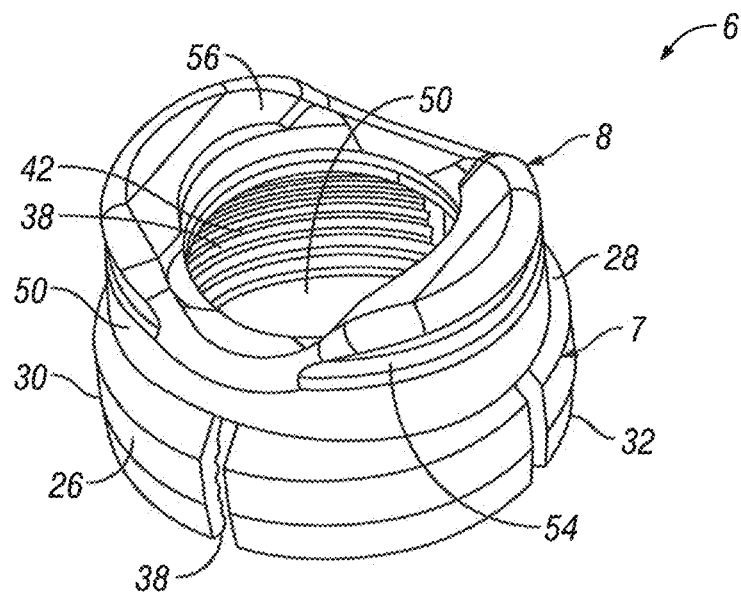
FIG. 2 is a perspective view of a locking clamp assembly in accordance with embodiments of the present invention.
Figure 3:
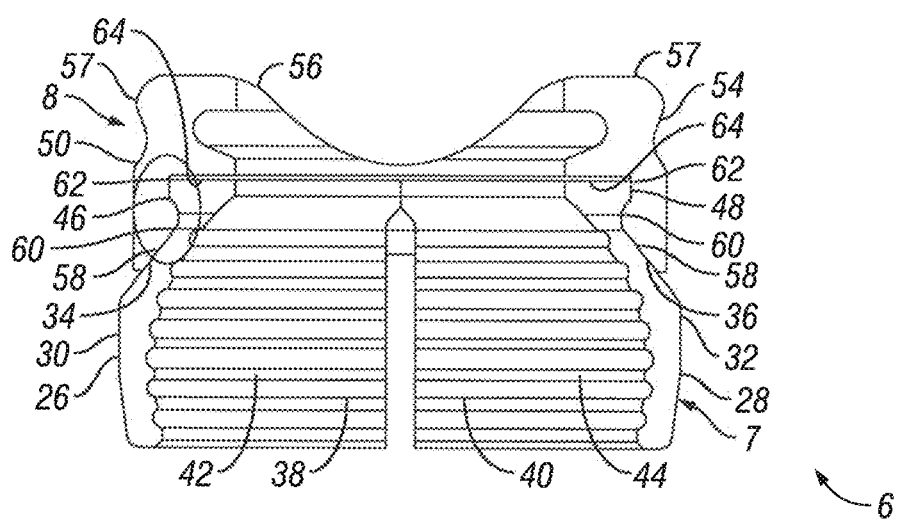
FIG. 3 is a cross-sectional view of a locking clamp assembly in accordance with embodiments of the present invention.

Referring now to FIGS. 1-3, clamp element 7 of the locking clamp assembly 6 will be described in more detail in accordance with embodiments of the present invention. As illustrated, the clamp element 7 includes a first clamp portion 26 and a second clamp portion 28. In the illustrated embodiment, the first clamp portion 26 is substantially identical to and a mirror image of, the second clamp portion 28. The first and second clamp portions 26, 28 provide a collar about the head 16 of the bone fastener 4, when installed, as discussed in more detail below. The first and second clamp portions 26, 28 grip bone fastener 4 when force is applied onto the clamp element 7 by the tulip element 10. While the embodiments that are described and illustrated generally describe the first and second clamp portions 26, 28 as substantially identical, the portions 26, 28 may be of varying size and are not required to be mirror images of one another. In addition, while the clamp element 7 is illustrated as having two clamp portions (first and second clamp portions 26, 28), the clamp element 7 may comprise more than two portions for gripping the bone fastener 4.

As illustrated, each of the first and second clamp portions 26, 28 includes an outer surface 30, 32, which may be curved or rounded, as best shown in FIGS. 1 and 2. The outer surfaces 30, 32 of the first and second clamp portions 26, 28 may each include an outer tapered surface 34, 36. In addition, the outer surfaces 30, 32 may each also have at least one slit 38 formed therein. The at least one slit 38 may, for example, allow the first and second clamp portions 26, 28 to constrict and securely engage the head 16 of the bone fastener 4. The outer surfaces 30, 32 should abut and engage the inner wedge surface 86 of the tulip element 10 when fully installed and locked in place in the tulip element 10 in accordance with present embodiments. With particular reference to FIG. 3, the first and second clamp portions 26, 28 each include inner surfaces 38, 40. When fully installed and locked in place in the tulip element 10, the inner surfaces 38, 40 should abut and engage the head 16 of the bone fastener 4 in accordance with present embodiments. The illustrated embodiment shows the inner surfaces 38, 40 having roughened or textured features 22 that improve engagement with the head 16 of the bone fastener 4. The first and second clamp portions 26, 28 each may also include an external lip 46, 48, which may be located above the outer tapered surfaces 34, 36, as best seen in FIG. 3. The first and second clamp portions 26, 28 each may also include an upper surface 31, 33, as best seen in FIG. 1.

Figure 4:
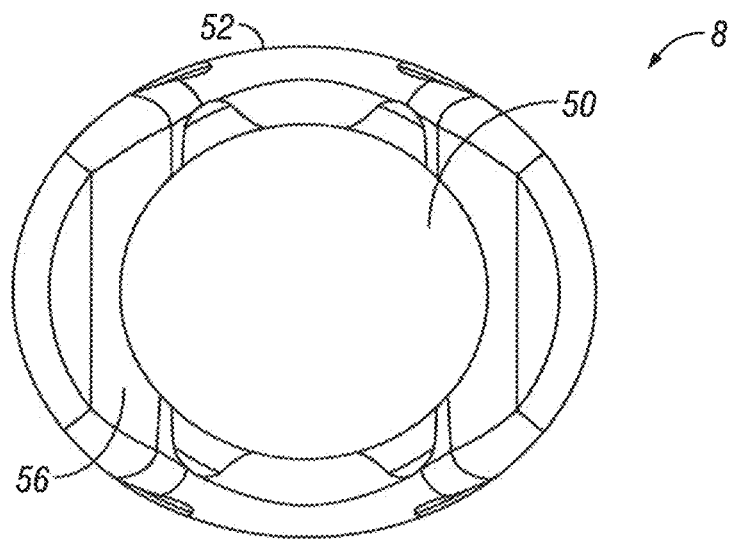
FIG. 4 is a top view of a wedge element in accordance with embodiments of the present invention.
Figure 5:
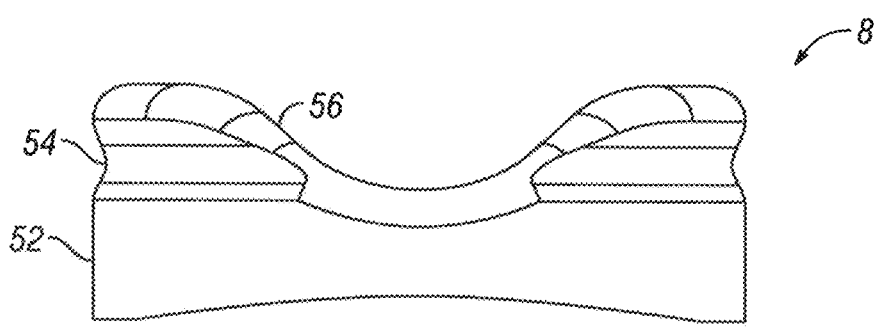
FIG. 5 is a side view of a wedge element in accordance with embodiments of the present invention.

Referring now to FIGS. 1-5, the wedge element 8 of the locking clamp assembly 6 will be described in more detail in accordance with embodiments of the present invention. As illustrated, the wedge element 8 may include a bore 50. The lower portion of the bore 50 may be sized to receive the upper portion of the clamp element 7, including external lips 46, 48 of the first and second clamp portions 26, 28. The wedge element further may include an outer surface 52 having a recessed portion 54. The outer surface 52 may be generally rounded, for example. As best seen in FIG. 4, the outer surface 52 of the wedge element 8 may be generally elliptical, in one embodiment. The elliptical shape of the outer surface 52 should, for example, limit radial motion of the wedge element when installed in the tulip element 10. The wedge element 8 further may include an upper surface 56. In the illustrated embodiment, the upper surface 56 defines a seat that receives the rod 14. As illustrated, the upper surface 56 may be generally convex in shape. In the illustrated embodiment, the wedge element 8 further includes an upper lip 57.

With particular reference to FIG. 3, the wedge element 8 further includes an inner wedge surface 58. As illustrated, the inner wedge surface 58 may be disposed around a lower portion of the bore 50. In one embodiment, the inner wedge surface 58 forms a conical wedge. The inner wedge surface 58 operates, for example, to engage the outer tapered surfaces 34, 36 of the first and second clamp portions 26, 28 to force the clamp element 7 down the bore 62 of the tulip element 10. The wedge element 8 further may include an inner protruding surface 60 adjacent to the inner wedge surface 58 and an inner recessed surface 62 adjacent the inner protruding surface 60. The wedge element 8 further may include an inner seat 64. As illustrated, the inner seat 64 may be downwardly facing for receiving upper surfaces 31, 33 of the first and second clamp portions 26, 28. In an embodiment, the inner seat 64 restricts or limits movement of the clamp element 4 through the bore 50 of the wedge element 8.

In accordance with present embodiments, the locking clamp assembly 6 can be assembled prior to insertion into the tulip element 10. In one embodiment, for assembly, the clamp element 7 may be inserted into the wedge element 8 upwardly through the bore 50. The outer surfaces 30, 32 of the first and second clamp portions 26, 28 should slidingly engage the inner wedge surface 58 of the wedge element 8 as the clamp element 7 is inserted. The clamp element 7 should be inserted until the external lips 46, 48 of the first and second clamp portions 26, 28 pass the inner protruding surface 60 of the wedge element 8. The inner protruding surface 60 engages the external lips 46, 48 to secure the clamp element 7 in the wedge element 8. In the illustrated embodiment, the locking clamp assembly 6 will not fit downwardly through the top of the bore 62 of the tulip element 10 as the locking clamp assembly has an outer diameter at its biggest point that is larger than the inner diameter of the upper portion of the bore 62.

Figure 6:
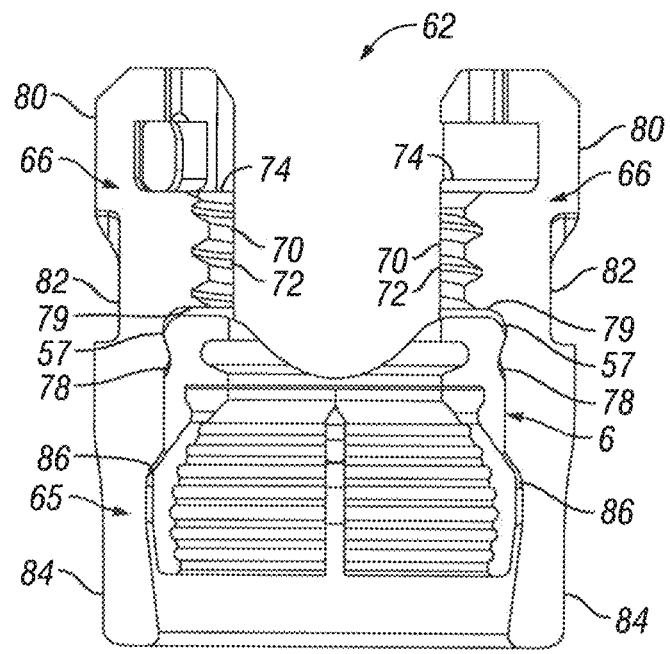
FIG. 6 is a cross-sectional view of a locking clamp assembly disposed in a tulip element in an unlocked configuration in accordance with embodiments of the present invention.
Figure 9:
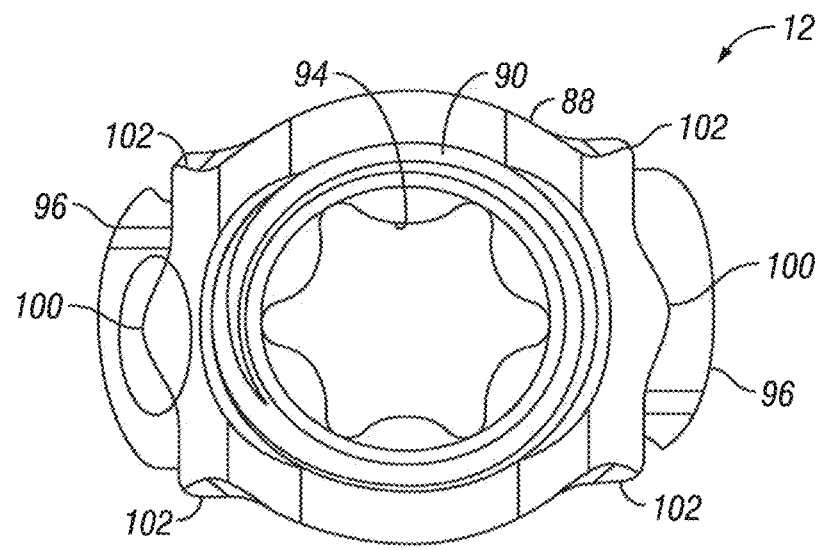
FIG. 9 is a top view of a locking cap assembly in accordance with embodiments of the present invention.
Figure 8:
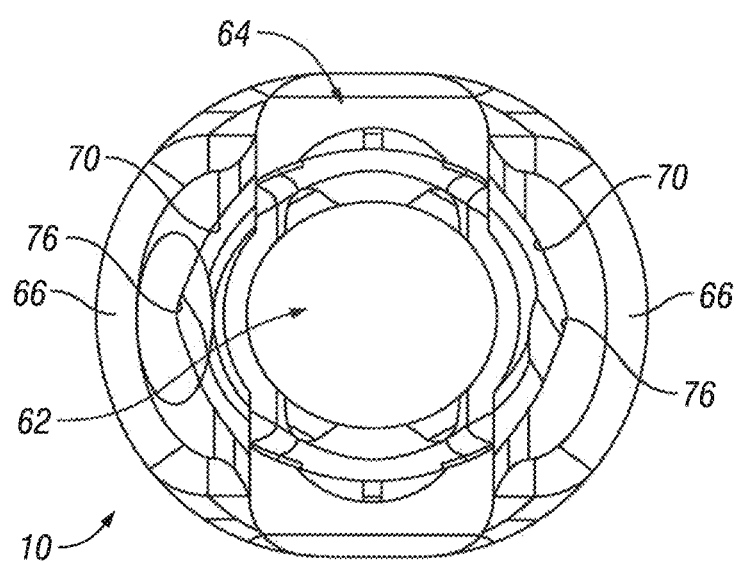
FIG. 8 is a top view of a tulip element in accordance with embodiments of the present invention.
Figure 10:
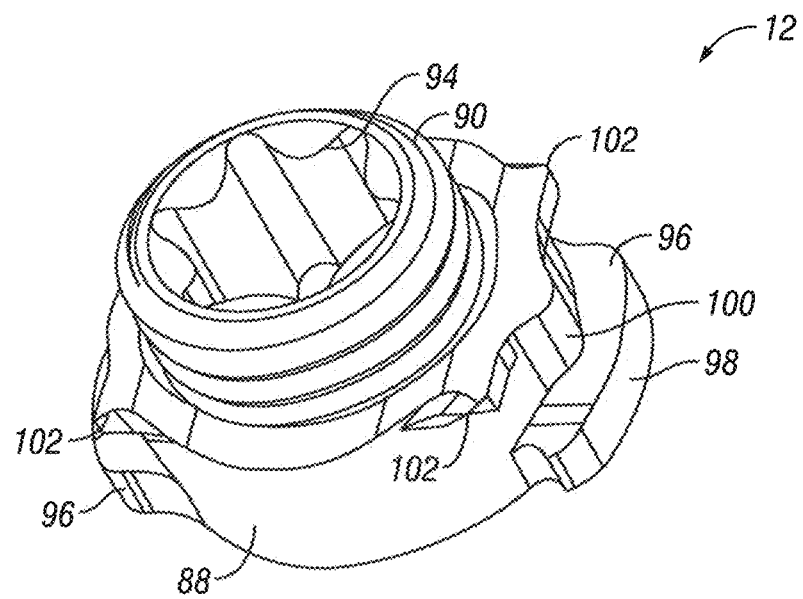
FIG. 10 is a perspective view of a locking cap assembly in accordance with embodiments of the present invention.
Figure 11:
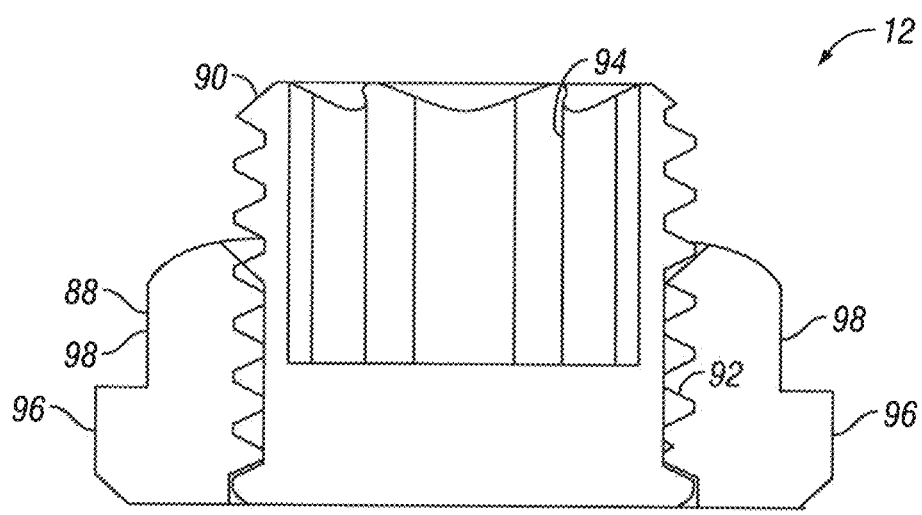
FIG. 11 is a cross-sectional view of a locking cap assembly in accordance with embodiments of the present invention.

Referring now to FIGS. 1 and 6-8, the tulip element 10 will be described in more detail in accordance with embodiments of the present invention. As illustrated, the tulip element 10 may comprise bore 62, a body 65 and arms 66 that extend upwardly from the body 65. In the illustrated embodiment, the arms 66 define a U-shaped channel 68 sized to receive the rod 14. Each of the arms 66 has an interior surface 70 the interior surface 70 having a threaded portion 72 for engaging corresponding threads on a screw-driving tool (e.g., tool 144 on FIGS. 27-29). The interior surface 70 of each of the arms 66 further may include a slot 74 for receiving corresponding tabs 96 (e.g., FIG. 9) of the locking cap assembly 12 and a recessed surface 76 for engaging corresponding protuberances 100 (e.g., FIG. 9) of the locking cap assembly 12. As illustrated, the recessed surface 76 of each of the arms 66 may be located above the slot 74. The interior surface 70 of each of the arms 66 further may include a protuberance 78. In the illustrated embodiment, the protuberance 78 of each of the arms 66 is located below the threaded portion 72 with the threaded portion 72 being located between the protuberance 78 and the slot 74. As best seen in FIG. 6, the interior surface 70 of each of the arms 66 further may form a downwardly facing seat 79, for example, which may limit or restrict movement of the locking clamp assembly 6 through the bore 62. Each of the arms 66 further may include an outer surface 80. The outer surface 80 of each of the arms 66 may include a tool engagement groove 82 formed on the outer surface 80 which may used for holding the tulip element 10 with a suitable tool (not illustrated).

Figure 7:
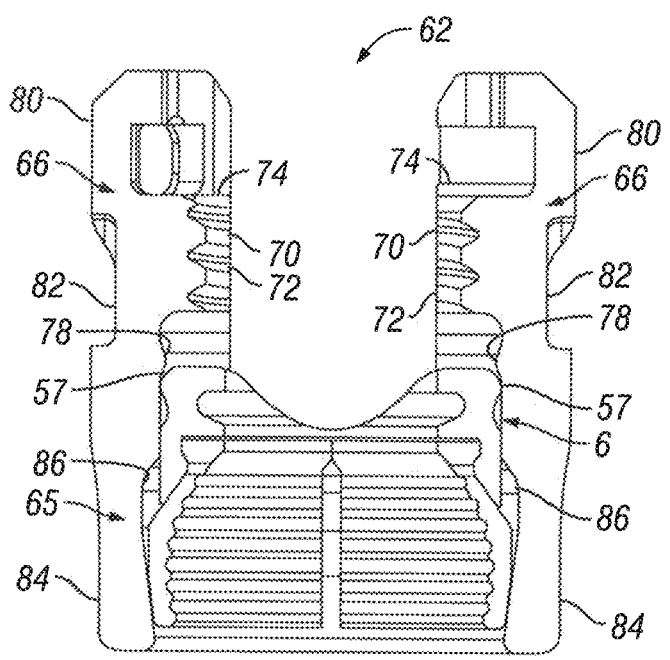
FIG. 7 is a cross-sectional view of a locking clamp assembly disposed in a tulip element in a locked configuration in accordance with embodiments of the present invention.

As illustrated, the body 65 of the tulip element 10 may have an outer surface 84, which may be curved or rounded, as best seen in FIG. 1. With particular reference to FIGS. 6 and 7, the body 65 further may include an inner wedge surface 86 disposed around a lower portion of the bore 62. In one embodiment, the inner wedge surface 86 forms a conical wedge. The inner wedge surface 86 of the body 65 of the tulip element 10, for example, may abut and engage the outer surfaces 30, 32 of the first and second clamp portions 26, 28 when the locking clamp assembly 6 is fully installed and locked in place.

In accordance with present embodiments, the locking clamp assembly 6 may be installed in the tulip element 10 in either an unlocked position or a locked position. FIG. 6 illustrates the locking clamp assembly 6 disposed in the tulip element 10 in the unlocked position in accordance with embodiments of the present invention. In FIG. 6, the locking clamp assembly 6 has been inserted into the tulip element 10 upwardly through the bore 62. The locking assembly 6 should be inserted until the upper lip 57 of the wedge element 8 passes the protuberances 78 located on the interior surfaces 70 of the arms 66 of the tulip element 10. The protuberances 78 should engage the upper lip 57 to secure the locking clamp assembly 6 in the tulip element 10. While not illustrated on FIG. 6, the bone fastener 4 (e.g., shown on FIG. 1) can now be placed into the locking assembly 6 through a snap fit with the clamp element 7. There should be sufficient clearance for the clamp element 7 to expand and snap around the head 16 of the bone fastener 4. The locking clamp assembly 6 and the tulip element 10, however, should still be free to rotate with respect to the bone fastener 4. The tulip element 10 can be moved and rotated to obtain a desired portion with respect to the bone fastener 4. The locking clamp assembly 6 should also move with the tulip element during rotation of the tulip element 10 with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 7 illustrates the locking clamp assembly 6 disposed in the tulip element 10 in the locked position in accordance with embodiments of the present invention. In FIG. 7, the locking clamp assembly 6 has been pushed downwardly in the bore 62 of the tulip element 10. As illustrated, the locking clamp assembly 6 has been pushed downward until the upper lip 57 of the wedge element 8 passes the protuberances 78 located on the interior surfaces 70 of the arms 66 of the tulip element 10. As the locking clamp assembly 6 moves downward, the clamp element 7 engages the body 65 of the tulip element 10. As illustrated, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 (e.g., FIG. 1). In the locked position, tulip element 10 should be locked onto the bone fastener 4, thus preventing further positioning of the tulip element 10 with respect to the bone fastener 4.

Referring now to FIGS. 1 and 9-11, the locking cap assembly 12 will be described in more detail in accordance with embodiments of the present invention. As illustrated, the locking cap assembly 12 may comprise a body 88 and a set screw 90 threaded into a bore 92 in the body 88. The set screw 90 may have a length, for example, that is longer than the length of the bore 92. In the illustrated embodiment, at least a portion of the set screw 90 extends from the top of the body 88. In certain embodiments, the set screw 90 may have a tool engagement surface, for example, that can be engaged by a screw-driving tool or other device. The tool engagement surface can permit the physician to apply torsional or axial forces to the set screw 90 to advance the set screw 90 through the body 88 and onto the rod 14. When the locking cap assembly 12 is in its locked position, the set screw 90 can be advanced through the body 88 to engage the rod 14, applying downward force onto the rod 14 and securing it to the tulip element 12. In one embodiment, the set screw 90 forces the rod 14 downward and into contact with the locking clamp assembly 6 causing the locking cap assembly 6 to move downward in the tulip element 10. In the illustrated embodiment, the tool engagement surface of the set screw 90 is a polygonal recess 94. For instance, the polygonal recess 94 may be a hexagonal recess that receives a hexagonal tool, such as an allen wrench, for example. The present invention is intended to encompass tool engagement surfaces having other shapes, such as slot or cross that may be used, for example, with other types of screwdrivers. In an alternative embodiment (not illustrated), the engagement surface may be configured with a protruding engagement surface that may engage with a tool or device having a corresponding recess.

In accordance with present embodiments, the body 88 may have one or more projections. For example, the body 88 may comprise lower tabs 96 projecting radially from a lower end of the body 88. In the illustrated embodiment, the body 88 comprises a pair of lower tabs 96 located on opposite sides of the body 88. As illustrated, the lower tabs 96 may each have an outer surface 98 that is generally rounded in shape. In addition, while the body 88 is illustrated as having two lower tabs 96, the body 88 may comprise more than two lower tabs 96. As illustrated, the body 88 further may comprise protuberances 100. The protuberances 100 may engage with corresponding recessed surface 76 (e.g., FIG. 10) of the arms 66 of the tulip element 10. The protuberances 100 may be capable of providing a tactile or audible signal to the physician, such as a click that may be felt or heard, when the locking cap assembly 12 has reached its locking position. The protuberances 100 also may assist in maintaining the locking cap assembly 12 in its locked position. In the illustrated embodiment, the body 88 further may comprise tool engagement features. The tool engagement features may, for example, be used for holding or manipulating the locking cap assembly 12 with a suitable tool (not illustrated). In the illustrated embodiment, the locking cap assembly 12 includes upper tabs 102. As illustrated, the tabs 102 may be formed at the upper surface of the body 88. In the illustrated embodiment, the locking cap assembly 12 includes four upper tabs 102 at the corners of the upper surface. In addition, while the body 88 is illustrated as having four upper tabs 102, the body 88 may comprise more or less than four upper tabs 102.

To place the locking cap assembly 12 onto the tulip element 10, the lower tabs 96 should be aligned with the u-shaped channel 68 formed by the arms 66 of tulip element 10 and the locking cap assembly 12 can then be lowered downward into the bore 62 in the tulip element 10. Once the lower tabs 96 are aligned with the corresponding slots 74 in the arms 66 of the tulip element 10, the locking cap assembly 12 can be rotated. The slots 74 allow the lower tabs 96 to pass through the arms 66 when the lower tabs 96 and the slots 74 are aligned. The length of the slots 74 generally correspond to the amount of rotation needed to move the locking cap assembly 12 into or out of a locked position. In one embodiment, the locking cap assembly 12 rotates from about 60° to about 120° for placement into a locking positions, alternatively, about 80° to about 100°, and, alternatively, about 90°. As previously mentioned, the protuberances 100 can be configured to provide a tactile or audible signal to the physician when the locking cap assembly 12 has reached its locked assembly. In addition, the protuberances 100 can also assist in maintaining the locking cap assembly 12 in its locked position. Other features such as undercuts and geometric mating surfaces may be used to prevent rotation in the opposite direction. With the locking cap assembly 12 locked in place, the set screw 94 can then be rotated. As the set screw 94 moves downward and extends from the bottom of the base 88 of the locking cap assembly 12, the set screw 94 presses against the rod 14 securing it in the tulip element 10. In addition, the rod 14 may also be pressed downward into engagement with the locking clamp assembly 6 forcing it downward in the tulip element 10. As the locking clamp assembly 6 moves downward, the clamp element 7 engages the body 65 of the tulip element 10. As best seen in FIG. 7, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4 and secure it with respect to the tulip element 10.

Referring now to FIGS. 12-14, locking of the tulip element 10 onto the bone fastener 4 is illustrated in more detail in accordance with embodiments of the present invention. For the purposes of this illustration, the locking cap element 12 (e.g., FIG. 1) is not shown. The tulip element 10 shown in FIGS. 12-14 is similar to the tulip element 10 described previously except that the tulip element 10 does not include a threaded portion 72 (e.g., FIGS. 6-7) or a downwardly facing seat 79 (e.g., FIG. 6) in the interior surface 70 of the arms 66 of the tulip element 10. FIG. 12 illustrates the locking clamp assembly 6 installed in the tulip element 10 in an unlocked position. As previously mentioned, the locking clamp assembly 6 can be inserted into the tulip element 10 upwardly through the bore 62. As shown in FIG. 12, the locking assembly 6 should be inserted until the upper lip 57 of the wedge element 8 passes the protuberances 78 located on the interior surfaces 70 of the tulip element 10. The protuberances 78 should engage the upper lip 57 to secure the locking clamp assembly 6 in the tulip element 10. As illustrated by FIG. 13, the bone fastener 4 can now be placed into the locking assembly 6 through a snap fit with the clamp element 7. There should be sufficient clearance for the clamp element 7 to expand and snap around the head 16 of the bone fastener 4. The locking clamp assembly 6 and the tulip element 10, however, should still be free to rotate with respect to the bone fastener 4. The tulip element 10 can be moved and rotated to obtain a desired portion with respect to the bone fastener 4. Once the tulip element 10 is at the desired position, the tulip element 10 may be locked onto the bone fastener 4. The locking clamp assembly 6 and the tulip element 10 should cooperate to lock the clamp assembly 6 onto the head 16 of the bone fastener 4.

FIG. 14 illustrates the locking clamp assembly 6 disposed in the tulip element 10 in the locked position and clamping onto the bone fastener 4 to secure the bone fastener 4 with respect to the tulip element 10 in accordance with embodiments of the present invention. As seen in FIG. 14, the locking clamp assembly 6 has been pushed downwardly in the bore 62 of the tulip element 10 until the upper lip 57 of the wedge element 8 passes the protuberances 78 located on the interior surfaces 70 of the arms 66 of the tulip element 10. As the locking clamp assembly 6 moves downward, the clamp element 7 engages the body 65 of the tulip element 10 such that the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to engage head 16 of the bone fastener 4. In the locked position, tulip element 10 should be locked onto the bone fastener 4, thus preventing further positioning of the tulip element 10 with respect to the bone fastener 4.

Figure 15:
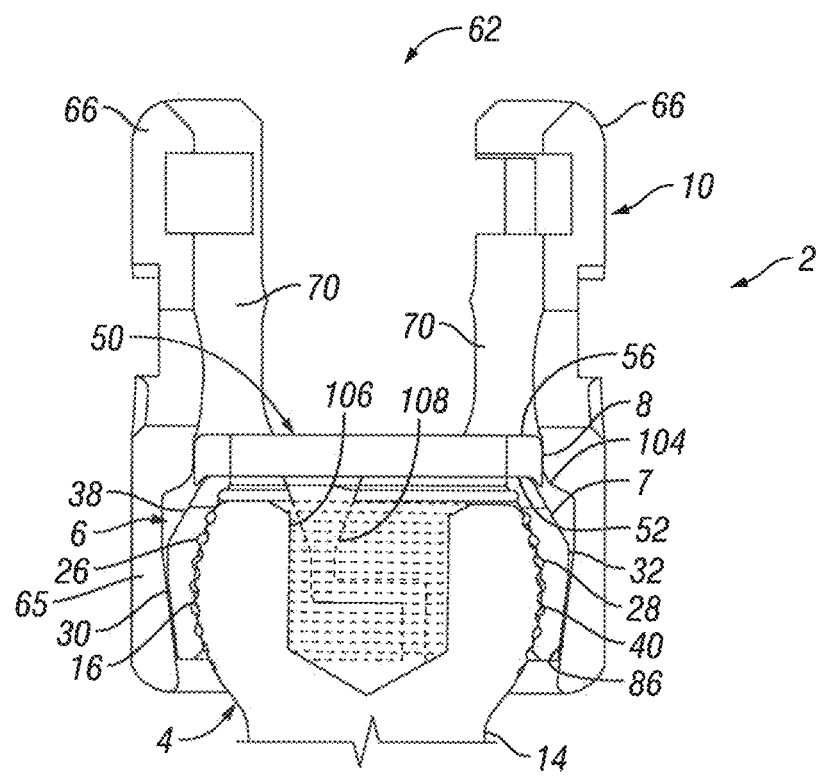
FIGS. 15-16 illustrate another alternative orthopedic fixation device in accordance with embodiments of the present invention.
Figure 16:
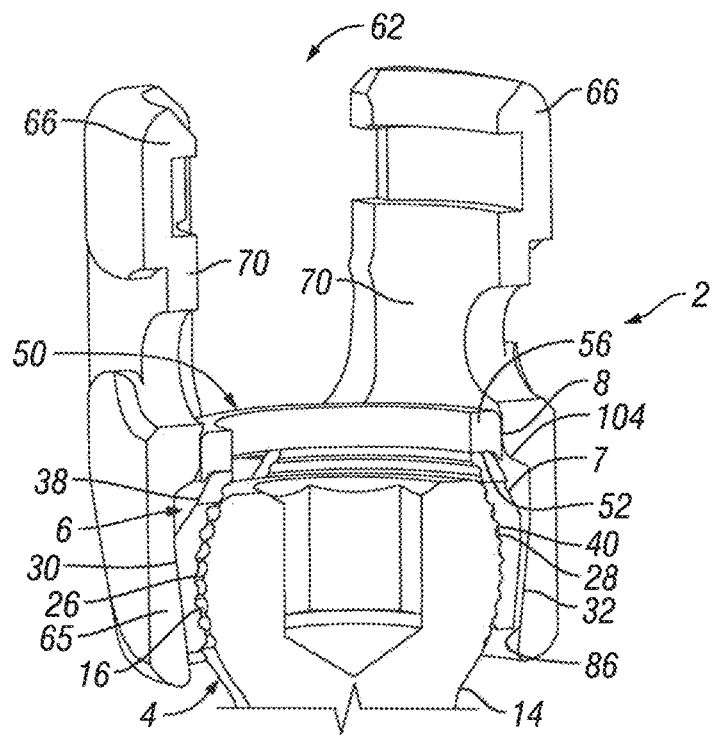

Referring now to FIGS. 15 and 16, an orthopedic fixation device 2 is described in accordance with alternative embodiments of the present invention. As illustrated, the orthopedic fixation device 2 comprises a bone fastener 4, locking clamp assembly 6, and a tulip element 10. For the purposes of this illustration, the locking cap assembly 12 (e.g., FIG. 1) is not shown. As previously mentioned, the locking clamp assembly 6 comprises a clamp element 7 and a wedge element 8.

As illustrated, the clamp element 7 may include a first clamp portion 26 and a second clamp portion 28. In the illustrated embodiment, the first and second clamp portions 26, 28 each include an inner tapered surface 106, 108 such that the lower portions of the first and second clamp portions 26, 28 can expand when pressure is applied that constricts the upper portion of the first and second clamp portions 26, 28. In contrast, to the wedge element 8 that was previously described, embodiments of the upper surface 56 of the wedge element 8 illustrated on FIGS. 15 and 16 do not define a seat that receives the rod 14 (e.g., FIG. 1), but rather are generally planar with bore 50 penetrating there through. As illustrated, the wedge element 8 further includes an inner wedge surface 58 formed around a lower portion of the bore 50. As also previously mentioned, the tulip element 10 generally may comprise a bore 62, base 64, and arms 66. The inner diameter of the bore 62 in the upper portion of the tulip element 10 may be made smaller than either the combined size of the clamp element 7 and the bone fastener 4 or the diameter of the shaft 14 of the bone fastener 4, whichever is larger. As illustrated, the arms 66 may each comprise an interior surface 70. In the illustrated embodiment, the interior surface 70 includes inner tapered surface 104 rather than a downwardly facing seat 79 (e.g., FIG. 6) in the interior surface 70 of the arms 66 of the tulip element 10.

With continued reference to FIGS. 15 and 16, locking of the tulip element 10 onto the bone fastener 4 will be described in more detail in accordance with embodiments of the present invention. The first and second clamp portions 26, 28 of the clamp element 7 may be inserted one after another upwardly into the bore 62 of the tulip element 10. The first and second clamp portions 26, 28 may be pushed axially towards the top of the tulip element 10. The first and second clamp portions 26, 28 should continue to move upwardly until they engage the inner tapered surface 104 of the tulip element 10. Due the taper angle of the inner tapered surface 104, the upper portion of the first and second clamp portions 26, 28 will be forced to move inwards until the inner tapered surfaces 106, 108 of each of the first and second clamp portions 26, 28 come into contact. This contraction at the top of the first and second clamp portions 26, 28 should result in a wider opening at the bottom of the clamp element 7. The bone fastener 4 can then be inserted through the bore 62 of the tulip element 10 and into the clamp element 7. The bone fastener 4 can then be manipulated, for example, to center the clamp element 7 into the head 16 of the bone fastener 4. The tulip element 10, however, should still be free to rotate with respect to the bone fastener 4. The tulip element 10 can be moved and rotated to obtain a desired portion with respect to the bone fastener 4. Once the tulip element 10 is at the desired position, the tulip element 10 may be locked onto the bone fastener 4.

To lock the tulip element 10, the bone fastener 4 can be pulled downward and because the clamp element 7 is in engagement with the bone fastener 4, the clamp element 7 should also move downward in the tulip element 10 such that the clamp element 7 engages the body 65 of the tulip element 10. As illustrated, the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to clamp onto the head 16 of the bone fastener 4. The wedge element 8 can then be introduced downwardly from the top of the bore 62 in the tulip element 10 to seat on top of the clamp element 7. The wedge element 8 should engage the interior surfaces 70 of the tulip element 10 preventing upward movement of the clamp element 7, locking the clamp element 7 in its engagement with the head 16 of the bone fastener. In the locked position, the tulip element 10 should be locked onto the bone fastener 4, thus preventing further positioning of the tulip element 10 with respect to the bone fastener 4.

Figure 17:
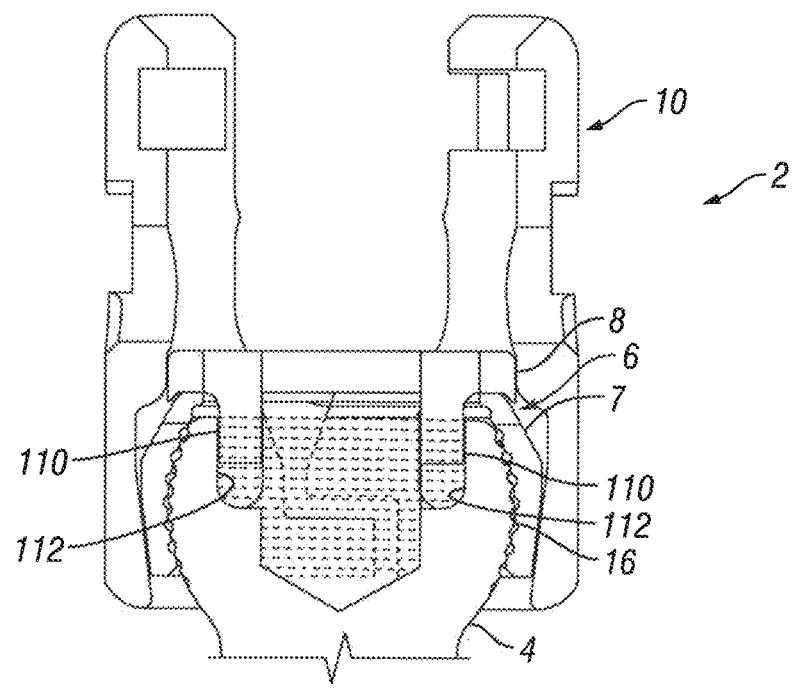
FIGS. 17-19 illustrate yet another alternative orthopedic fixation device in accordance with embodiments of the present invention.
Figure 18:
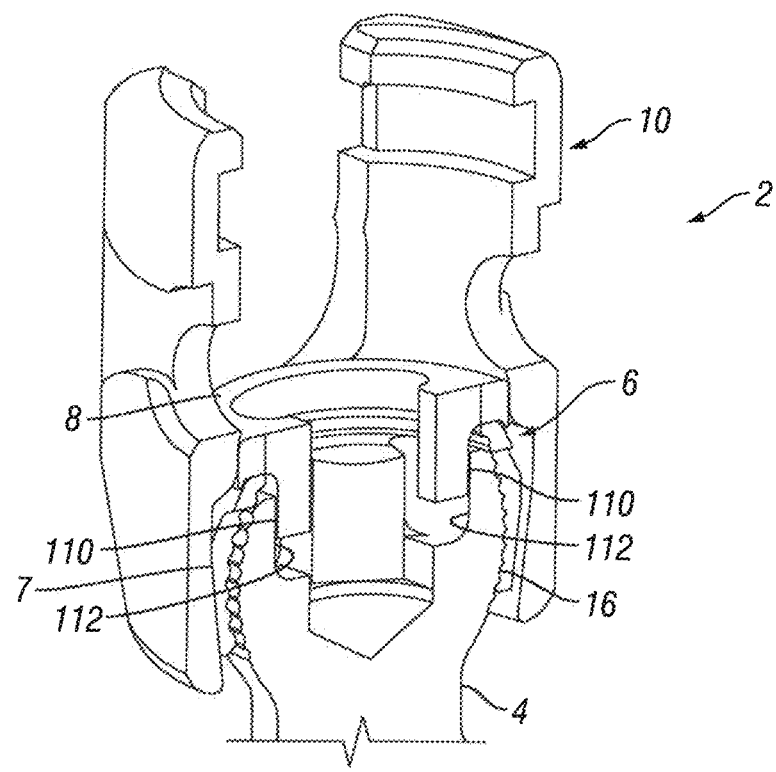
Figure 19:
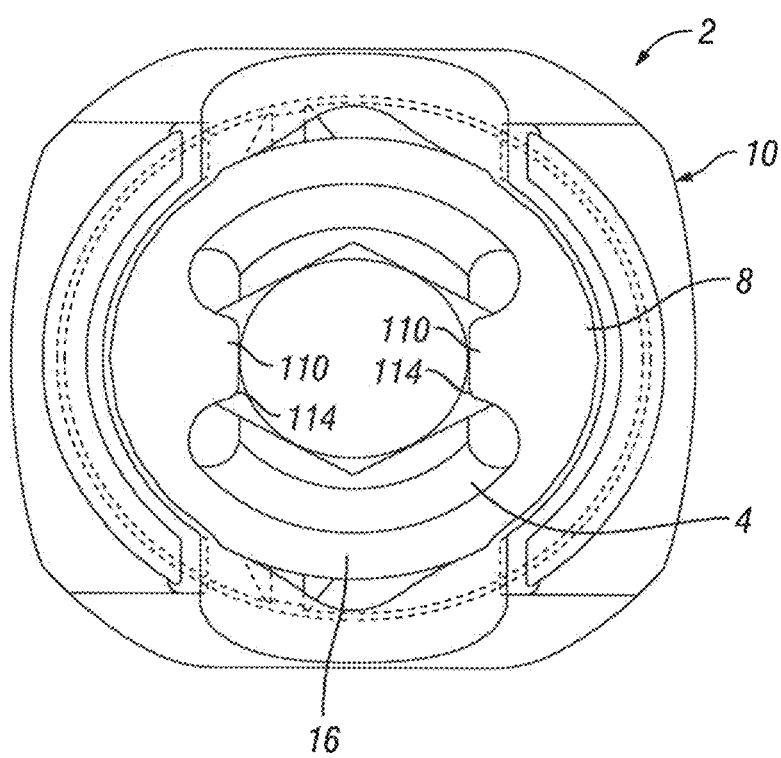

Referring now to FIGS. 17-19, an orthopedic fixation device 2 is described in accordance with alternative embodiments of the present invention. As illustrated, the orthopedic fixation device 2 comprises a bone fastener 4, a locking clamp assembly 6, and a tulip element 10. For the purposes of this illustration, the locking cap assembly 12 (e.g., FIG. 1) is not shown. In the illustrated embodiment, the locking clamp assembly 6 comprises a clamp element 7 and a wedge element 8. The orthopedic fixation device 2 is similar to the embodiments of FIGS. 15-16 except that embodiments of the wedge element 8 include downwardly extending tabs 110 that fits into corresponding slots 112 in the top of the head 16 of the bone fastener 4. In general, the tabs 110 should impart a uni-planar restraint on the bone fastener 4 so that it only slides along mating surfaces. The interior surfaces 114 of the tabs 110, best seen in FIG. 19, should forms the sides of the internal driving features. In an alternative embodiment (not illustrated), the wedge element 8 can be configured so that the tabs 110 are interconnected, for example, to impart more strength to the design of the wedge element 8.

Referring now to FIGS. 20-21, an orthopedic fixation device 2 is described in accordance with alternative embodiments of the present invention. As illustrated, the orthopedic fixation device 2 comprises a bone fastener 4, a locking clamp assembly 6, and a tulip element 10. For the purposes of this illustration, the locking cap assembly 12 (e.g., FIG. 1) is not shown. In the illustrated embodiment, the locking clamp assembly 6 comprises a clamp element 7 and a wedge element 8.

The orthopedic fixation device 2 is similar to the embodiments of FIGS. 15-16 except that embodiments of the clamp element 7 are configured for top loading from the top of the bore 62 in the tulip element 10. Instead of being inserted upwardly from the bottom of the bore 62, the first and second clamp portions 26, 28 of the clamp element 7 are inserted downwardly from the top of the bore 62, until the clamp portions 26, 28 engage the inner wedge surface 86 of the body 65 of the tulip element 10. The bone fastener 4 can then be inserted upwardly from the bottom of the bore 62 of the tulip element 10 and into engagement with the clamp element 7 whereby the clamp element 7 will be pushed upwardly towards the top of the tulip element 10. The clamp element 7 will move higher until they engage an external temporary stop (not illustrated) that prevents further upward movement. As the clamp element 7 moves higher in the tulip element 10, the clamp portions 26, 28 adjust and reorient due to increased clearance with the inner wedge surface 86 of the tulip element 10 such that the opening at the bottom of the clamp element 7 is larger than the diameter of the head 16 of the bone fastener 4.

To lock the tulip element 10, the bone fastener 4 can be pulled downward and because the clamp element 7 is in engagement with the bone fastener 4, the clamp element should also move downward in the tulip element 10 such that the outer surfaces 30, 32 of the first and second clamp portions 26, 28 of the clamp element 7 should abut and engage the inner wedge surface 86 of the body 65 of the tulip element 10, forcing inner surfaces 38, 40 of the first and second clamp portions 26, 28 to clamp onto the head 16 of the bone fastener 4. In accordance with present embodiments, the smallest inner diameter for the bore 62 in the tulip element 10 is smaller than the combined size of the clamp element 7 and the head 16 of the bone fastener 4, when in engagement. The wedge element 8 can then be introduced downwardly from the top of the bore 62 in the tulip element 10 to seat on top of the clamp element 7. The wedge element 8 should engage the interior surfaces 70 of the tulip element 10 preventing upward movement of the clamp element 7, locking the clamp element 7 in its engagement with the head 16 of the bone fastener. In the locked position, the tulip element 10 should be locked onto the bone fastener 4, thus preventing further positioning of the tulip element 10 with respect to the bone fastener 4.

Figure 22:
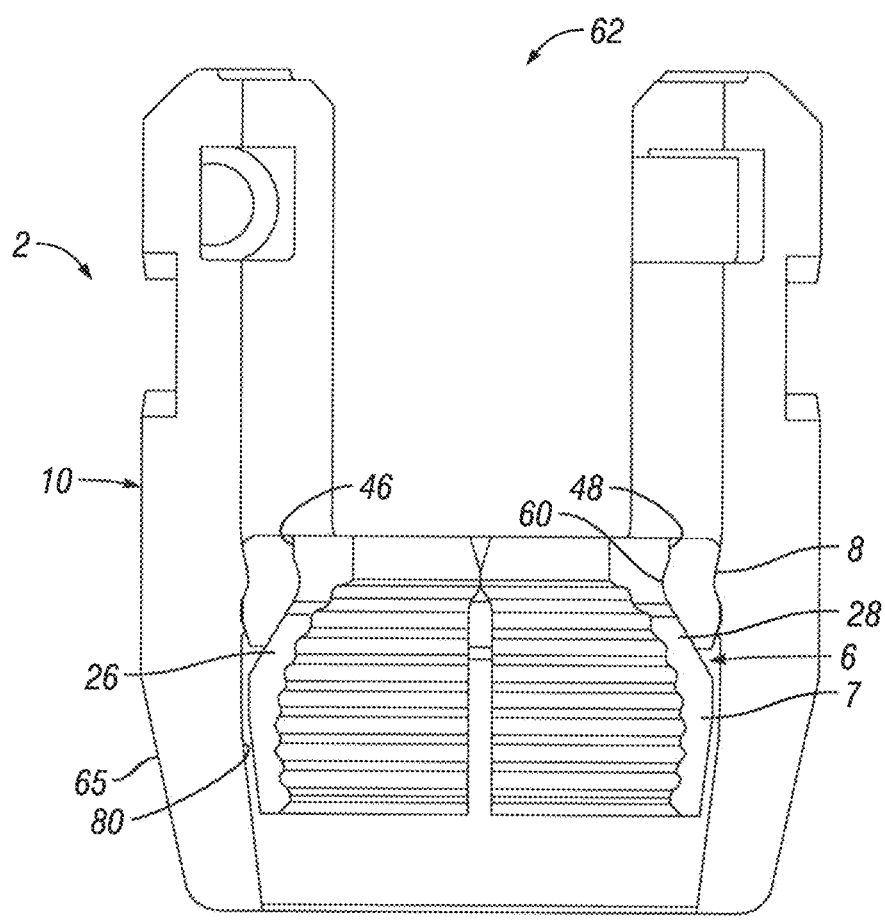

Referring now to FIG. 22, an orthopedic fixation device 2 is described in accordance with alternative embodiments of the present invention. As illustrated, the orthopedic fixation device 2 comprises a locking clamp assembly 6 and a tulip element 10. For the purposes of this illustration, the bone fastener (e.g., FIG. 1) and locking cap assembly 12 (e.g., FIG. 1) are not shown. In the illustrated embodiment, the locking clamp assembly 6 comprises a clamp element 7 and a wedge element 8.

The orthopedic fixation device 2 is similar to the embodiments of FIGS. 20-21 except that embodiments of the wedge element 8 include a retention feature for coupling with the clamp element 7. As illustrated, the wedge element 8 includes an inner protruding surface 60 that engages with the external lips 46, 48 of the first and second clamp portions 26, 28 of the clamp element 7 to secure the clamp element 7 in the wedge element 8. The locking clamp assembly 6 with the clamp element 7 secured in the wedge element 8 can then be inserted downwardly from the top of the bore 62 in the tulip element 10, until the clamp portions 26, 28 engage the inner wedge surface 86 of the body 65 of the tulip element 10. Once the bone fastener 4 is snapped into the clamp element 7, the locking clamp assembly 6 can be forced downwards through the tulip element 10 into its locked position to secure the bone fastener (e.g., FIG. 1) in the clamp element 7. In the locked position, the tulip element 10 should be locked onto the bone fastener 4, thus preventing further positioning of the tulip element 10 with respect to the bone fastener 4.

Figure 23:
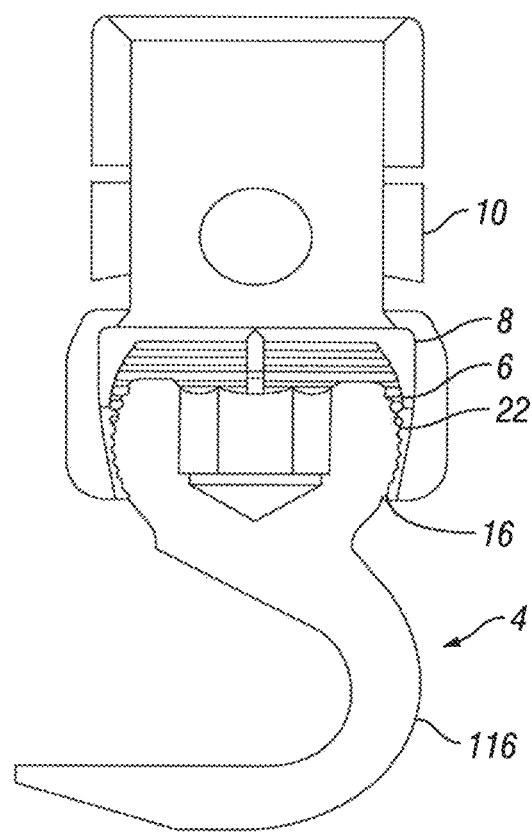
FIG. 23 illustrates an orthopedic fixation device comprising a bone hook in accordance embodiments of the present invention.

While the embodiments that are described and illustrated above generally illustrate a bone fastener 4 in shape of a screw having a head 16 and shaft 18 extending there from, it should be understood that other bone fasteners may also be used such as hooks and sacral blocks. Thus, the present invention may be used with a wide variety of bone fasteners in addition to a bone screw, as described above. For example, FIG. 23 illustrates an embodiment in which the bone fastener 14 includes a head 16 having an extension in the form of a hook 116 that extends from the head 16. In the illustrated embodiment, the head 16 is secured in the tulip element 10 by the clamp element 7 and the wedge element 8. As illustrated, the head 16 may have a roughened or textured surface 22 that improves engagement with the clamp element 7.

Figure 24:
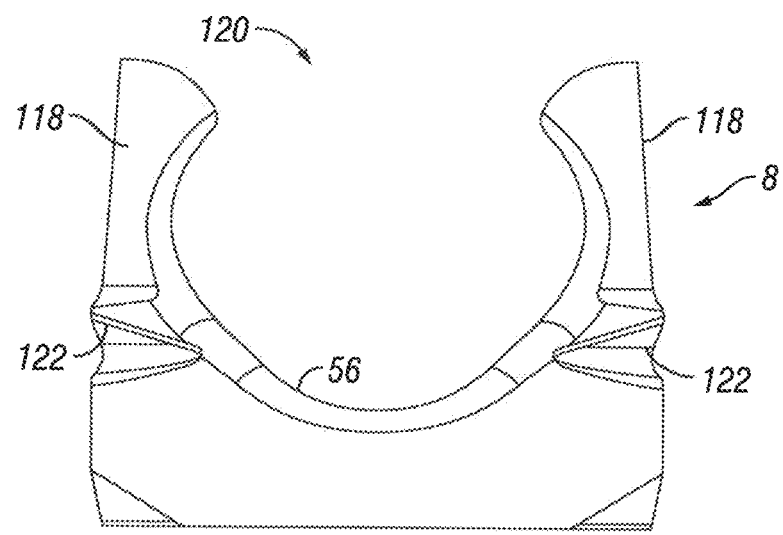
FIGS. 24-25 illustrate an alternative wedge element in accordance with embodiments of the present invention.
Figure 25:
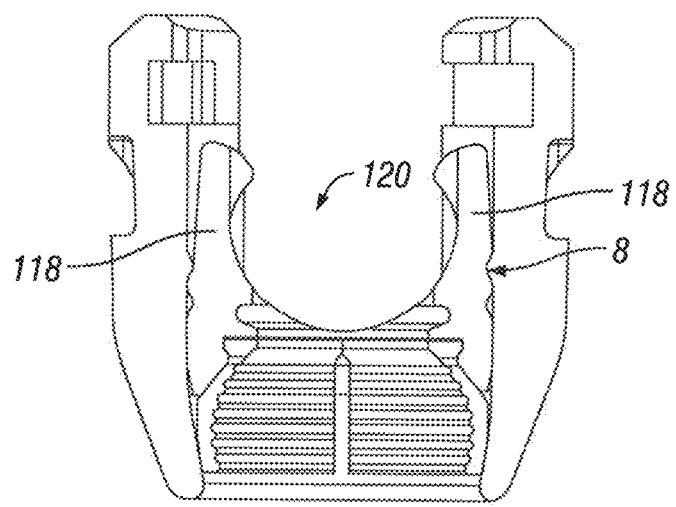

FIGS. 24 and 25 illustrate a wedge element 8 having an optional rod retention feature, in accordance with embodiments of the present invention. In some embodiments, the rod retention feature of the wedge element 8 may be added to enhance retainment of the rod 14 (e.g., FIG. 1) in a surgical procedure. In the illustrated embodiment, the rod retention feature is in the form of seat extensions 118 that will cradle the rod 14 to retain it in the wedge element 8. As illustrated, the wedge element 8 comprises an upper surface 56 defining a seat for receiving the rod 14. The wedge element 8 further may comprise seat extensions 118 for retaining the rod 14 in the wedge element 8. In one embodiment, the seat extensions 118 may be configured to flex when a rod 14 is pushed down through opening 122 at the top of the seat extensions 118. When pressed down, the rod 14 may engage the ends of the seat extensions 118 causing the seat extensions 118 to flex outward increasing the size of the opening so that the rod 14 can be moved downwards to rest on the upper surface 56 of the wedge element 8. In other words, the rod 14 may be snapped past the seat extensions 118 in accordance with some embodiments. In the illustrated embodiment, the wedge element 8 further includes notches 122 to facilitate flexing of the seat extensions 118.

While the embodiments that are described and illustrated above generally illustrate a tulip element 10 in the general shape of a "U" for coupling the rod 14 to the bone fastener 4, it should be understood that any of a variety of different coupling elements may be used in accordance with embodiments of the present invention. For example, the coupling element may be open (e.g., tulip element 10 on FIG. 1) or closed. In some embodiments, the rod 14 may be top loaded into an open coupling element. In other embodiments, the rod 14 may be side loaded, for example, into a closed coupling element. In some embodiments, the coupling element may be an open, closed, or offset iliac connector. In yet other embodiments, the coupling element may be a posted screw connector. In addition, the coupling element may be configured to move polyaxially, monoaxially, or uni-planar with respect to the bone fastener 4 prior to locking of the coupling element onto the bone fastener 4.

Figure 26:
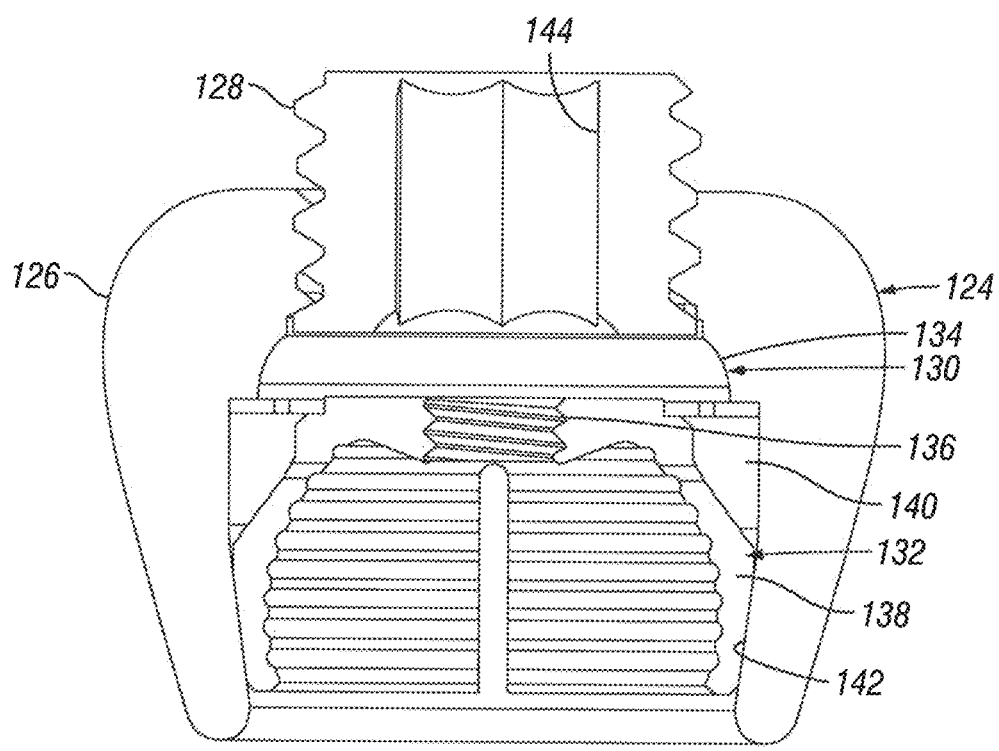
FIG. 26 illustrates an offset iliac connector in accordance with embodiments of the present invention.

FIG. 26 illustrates a coupling element in accordance with alternative embodiments of the present invention. In the illustrated embodiment, the coupling element is an offset iliac connector 124. The offset iliac connector 124 should allow, for example, iliac screw placement prior to selection of coupling element type. The design of the offset iliac connector 124 should also allow, for example, removal of the iliac connector 124 using a specialized instrument (not illustrated) to change the coupling element type in situ. As illustrated, the offset iliac connector 124 includes an offset housing 126, a set screw 128, a spring washer 130, and a locking clamp assembly 132. In accordance with embodiments of the present invention, the set screw 128 can be installed through the bottom of the offset housing 126 and rotated (e.g., counter clockwise) until tight. After installation of the set screw 128, the spring washer 130 may then be inserted upwardly through the bottom of the offset housing 126. In the illustrated embodiment, the spring washer 130 has a washer portion 134 and a spring portion 136 that extends down from the washer portion 134. The locking clamp assembly 132 may then be inserted upwardly through the bottom of the offset housing 126 and snapped into a place, in a manner similar to the previously described embodiments. In the illustrated embodiment, the locking clamp assembly 132 includes a wedge element 138 and a clamp element 140. To engage the offset connector with a head 16 of a bone fastener 4 (e.g., FIG. 1), the offset connector can be pushed down onto the head 16. The head 16 of the bone fastener 4 should be pushed upward into the locking clamp assembly 132. The bone fastener 4 should push the locking clamp assembly 132 upward into the spring portion 136 of the spring washer 130 until sufficient clearance is achieved between the locking clamp assembly 132 and the offset housing 126 for the bone fastener 4 to snap into the locking clamp assembly 132. The spring washer 130 should then provide downward force onto the locking clamp assembly 132 such that the interior wedge surface 142 of the offset housing 126 applies pressure to the locking clamp assembly 132 forcing the clamp element 138 to clamp onto the head 16 of the bone fastener 4. In some embodiments, a specialized instrument (not illustrate) can be threaded through the polygonal recess 144 (e.g., a hexagonal recess) in the set screw 128 and into the locking clamp assembly 132. The threading of the instrument should provide sufficient clearance with the offset housing 126 for removal of the offset iliac connector 124 from the bone fastener 4 without removal of the bone fastener 4 from the bone.

Figure 29:
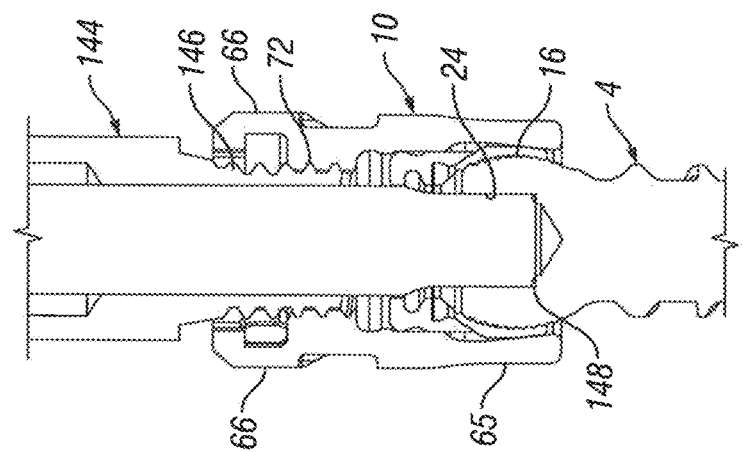
FIGS. 27-29 illustrate a bone fastener having a threaded instrument interface in accordance with embodiments of the present invention.
Figure 28:
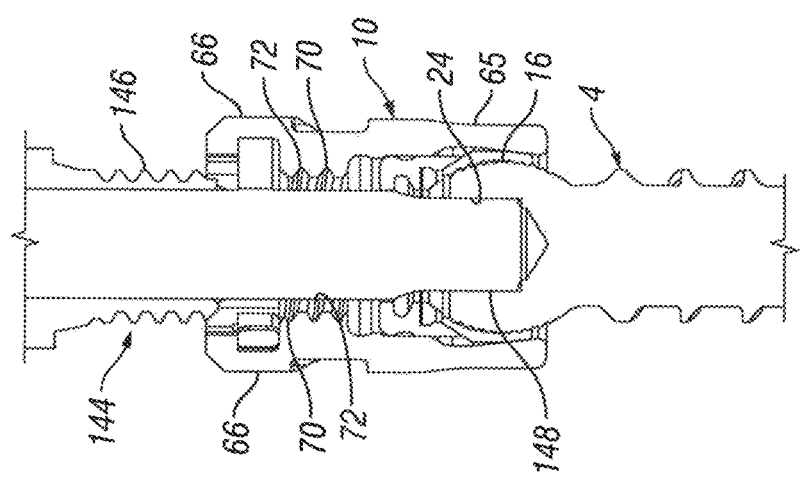
Figure 27:
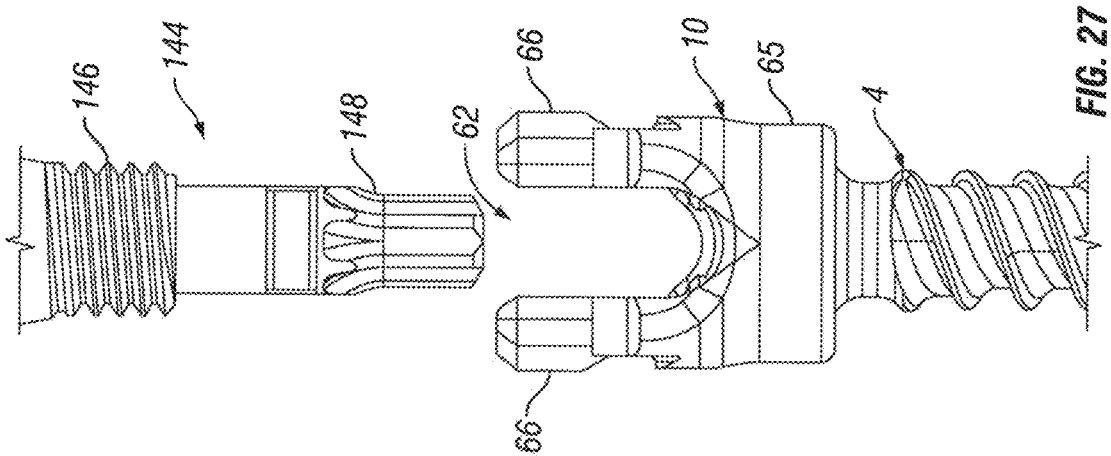

As previously illustrated and described with respect to FIG. 1, the tulip element 10 may include a threaded portion 72. FIGS. 27-29 illustrate the threaded portion 72 of the tulip element 10 in more detail. As illustrated, the tulip element 10 includes a body 65 and arms 66. As best seen in FIG. 28, the arms 66 each include an interior surface 70 having a threaded portion 72. In accordance with present embodiments, a bone fastener 4 can be secured to the tulip element 10. As illustrated, a tool 144, which may be, for example, a screw-driving tool, can be placed through the bore 62 in the tulip element 10 and into engagement with the tulip element 10 and the bone fastener 4. In the illustrated embodiment, the tool 144 includes a threaded portion 146 that engages the threaded portion 72 of the tulip element 10. The tool 144 further includes an engagement end 148 below the threaded portion 72 that engages with the polygonal recess 24 (e.g., hexagonal) in the head 16 of the bone fastener 4. In this manner, a rigid connection may be formed between the bone fastener 4 and the tool 144.

Figure 30:
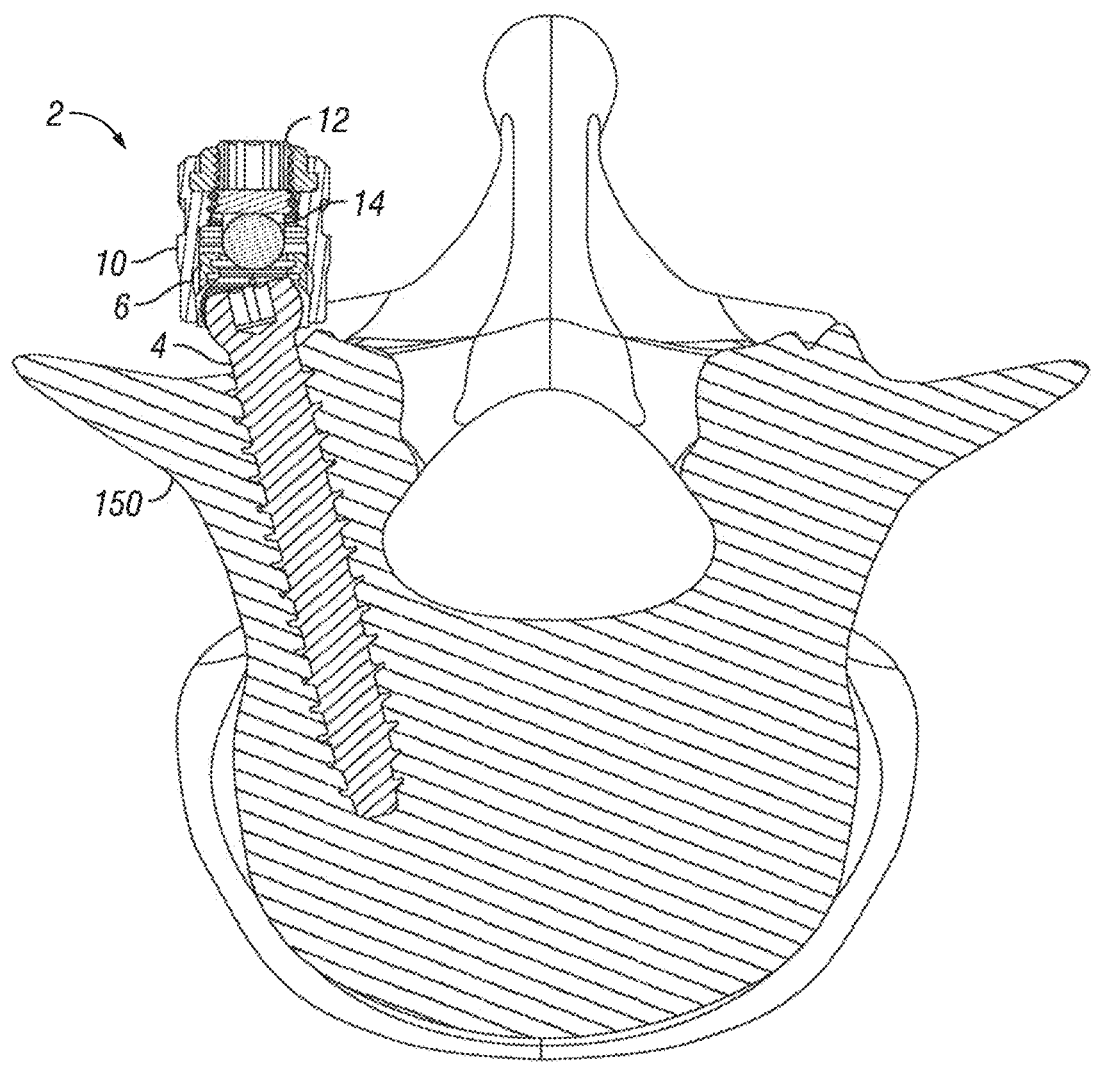
FIG. 30 illustrates a cross-sectional view of a vertebra having an orthopedic fixation device installed therein in accordance with embodiment of the present invention.

FIG. 30 illustrates installation of the orthopedic fixation device 2 in a vertebra 150 in accordance with embodiments of the present invention. As illustrated, the bone fastener 4 may be implanted into the vertebra 150. The bone fastener 4 may then be secured to the tulip element 10 using, for example, the locking clamp assembly 6. The tulip element 10 can then be moved and rotated into a desired position with respect to the bone fastener 4 and then locked onto the bone fastener 4. In one embodiment, the tulip element 10 is fixed onto the bone fastener 4 contemporaneously with securing the rod 14 to the tulip element 10 with the locking cap assembly 12. In this manner, the rod 14 can be secured in a fixed position relative to the vertebra 150.

Figure 31:
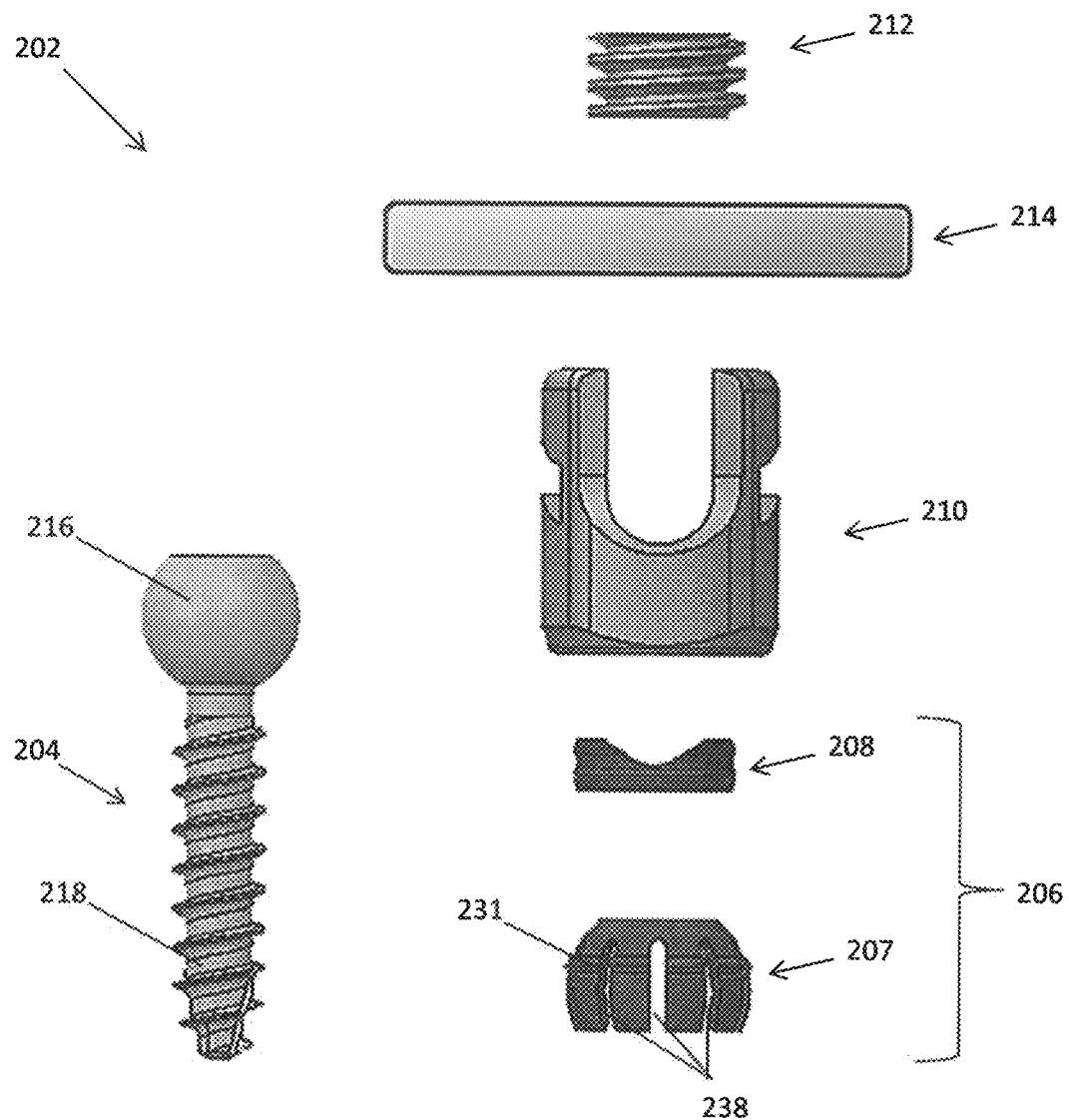
FIG. 31 is an exploded view of an orthopedic fixation device in accordance with embodiments of the present invention.

Turning now to FIGS. 31-36, an alternative embodiment of orthopedic fixation device 202 is illustrated. FIG. 31 provides an exploded view of the orthopedic fixation device 202. As illustrated, the orthopedic fixation device 202 may comprise a bone fastener 204, a locking clamp assembly 206 including clamp element 207 and wedge element 208, a tulip element 210, elongate rod 214, and threaded locking cap 212. This embodiment may be particularly suitable for posterior cervical or posterior cervico-thoraco constructs due to the increased angulation of the tulip element 210 relative to the bone fastener 204. In this embodiment, up to 100 degrees of conical angulation of the bone fastener 204 relative to the tulip element 210 may be obtained. The bone fastener 204 may be loaded from the bottom of the tulip element 210 with the locking clamp assembly 206 already loaded therein. Prior to being locked into place, the tulip element 210 can be freely moved and rotated into a plurality of positions with respect to the bone fastener 204.

The bone fastener 204 includes a head 216 and a threaded shaft 218 that extends from the head 216. In this embodiment, the head 216 is substantially smooth and is shaped to form a portion of a ball or at least a portion of a sphere. The threaded shaft 218 has a blunt tip and a compound taper. Two thread cutting flutes may be provided for self-tapping. The screw head 216 may include a driving recess 224 as described elsewhere herein, e.g., a hexalobular recess, for screw insertion.

Figures 32, 33:
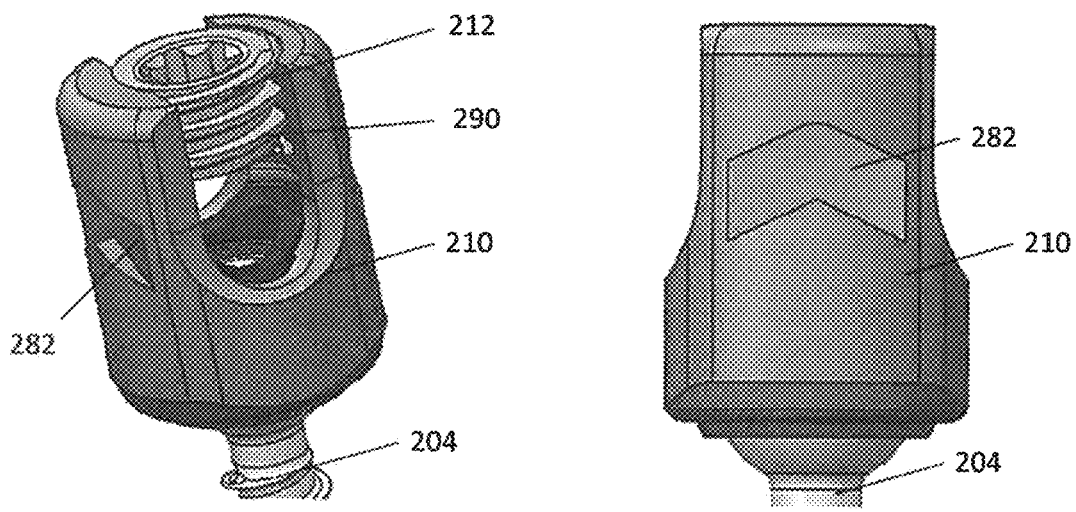
FIG. 32 is a perspective view of the orthopedic fixation device shown in FIG. 31, when assembled without the elongate rod.
FIG. 33 is a side view of the orthopedic fixation device shown in FIG. 31, when assembled without the elongate rod.
Figure 34:
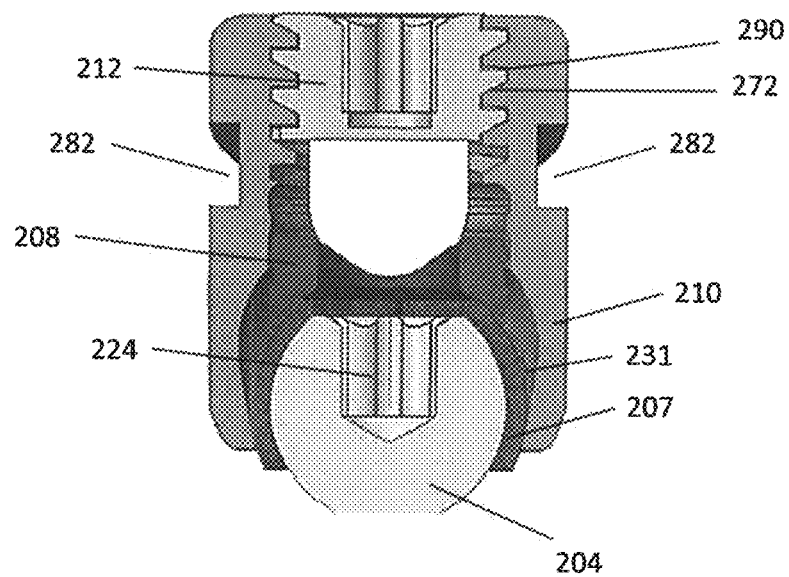
FIG. 34 is a cross-sectional view of the orthopedic fixation device shown in FIG. 31, when assembled without the elongate rod.

The tulip element 210, similar to tulip element 10, may be sized and configured to receive elongate rod 214 therein. For example, the tulip element 210 may be sized to receive a 3.5 mm or 4.0 mm diameter rod. As best seen in FIG. 34, an interior surface of the tulip element 210 may have a threaded portion 272 for engaging corresponding threads 290 on the threaded locking cap 212. Thus, the threaded locking cap 212 may be secured directly to the tulip element 210, for example, by rotating the locking cap 212 into a top portion of the tulip element 210 and engaging threads 272. As best seen in FIG. 33, one or more indentations 282, such as chevron type indentations, may be provided on an outer surface of the tulip element 210 for attachment of reduction instruments or the like (not illustrated).

In the orthopedic fixation device 202, a mating surface between the clamp element 207 and the tulip element 210 is substantially spherical rather than tapered or conical. The spherical outer diameter and spherical inner diameter of the clamp element 207 allow rotation of the clamp element 207 relative to both the tulip element 210 and the bone fastener 204. As best seen in FIG. 31, the clamp element 207 is a one-piece design having slits or relief cuts 238 therein. The relief cuts 238 may be uniformly or non-uniformly spaced around the perimeter of the clamp element 207. The relief cuts 238 may extend from a bottom portion of the clamp element 207 to a position proximate to a top portion of the clamp element 207 without extending completely therethrough. The relief cuts 238 in the clamp element 207 allow clamp fingers defined between each of the relief cuts 238 to be compressed upon insertion into the tulip element 210 and expanded upon insertion of the bone fastener 204 into the clamp element 207. A protrusion, bump, lip, or rim 231 in the outer profile of the clamp element 207 may be configured to act as a stop to limit rotation travel within the tulip element 210. The rim 231 may extend transverse to the relief cuts 238. The relief cuts 238 may extend through and beyond the rim 231 on the spherical outer surface of the clamp element 207. The clamp element 207 may be assembled from the bottom of the tulip element 210 and retained within the tulip element 210 prior to introducing the bone fastener 204.

The wedge element 208 includes an upper surface that defines a seat configured to receive the rod 214 and a lower surface that is configured to contact and receive the clamp element 207. The wedge element 208 is captured by an elliptical profile inner diameter of the tulip element 210. This profile keys the wedge element 208 to a specific orientation to the tulip element 210. A v-notch in the upper surface of the wedge element 208 may allow for the rod 214 to have at least two points of contact, thereby adding stability to the assembly when locked. A spherical diameter of the wedge element 208 contacts a spherical diameter on the clamp element 207 and retains the clamp element 207 in the tulip element 210. As the locking cap 212 is tightened down, the rod 214 will apply pressure to the wedge element 208 to lock the clamp element 207 and bone fastener 204 in position.

Figure 35:
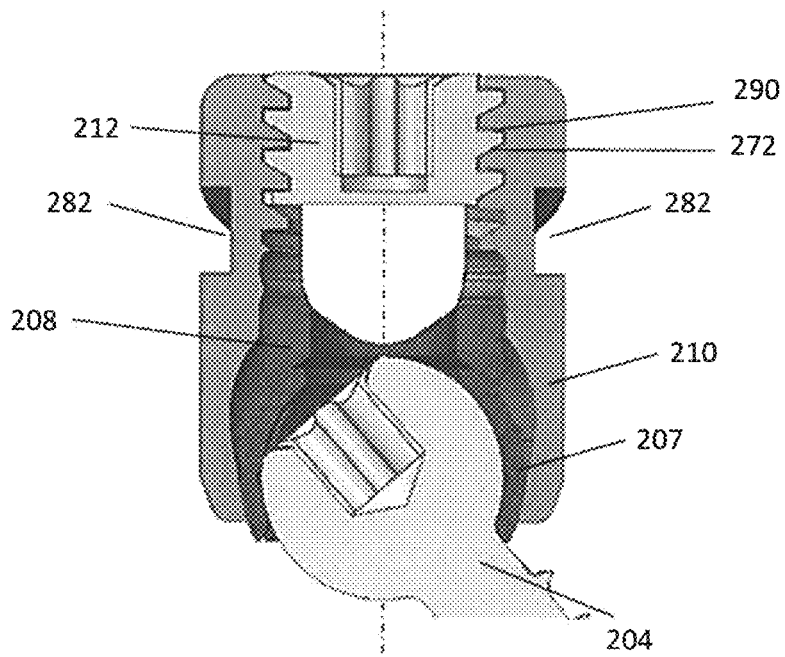
FIG. 35 is a cross-sectional view depicting angulation of the screw.
Figure 36:
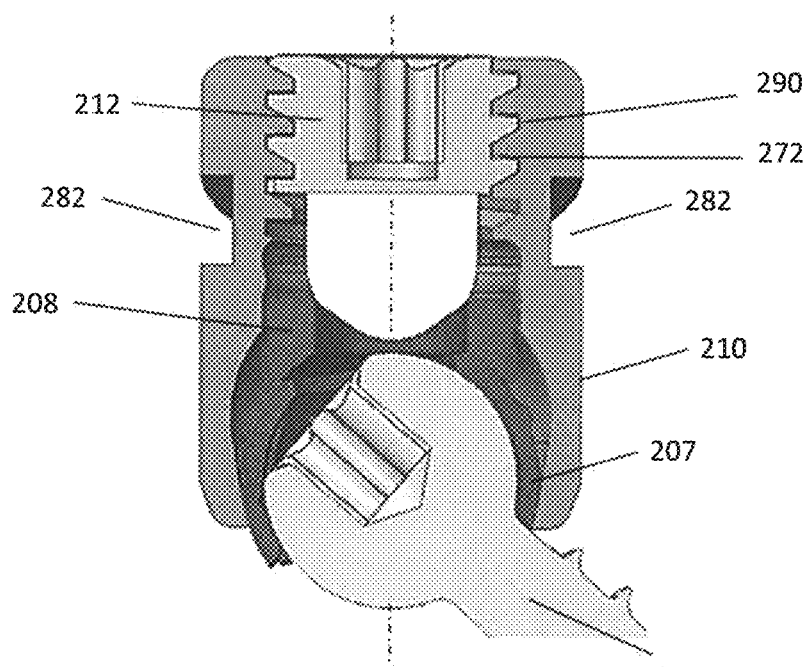
FIG. 36 is a cross-sectional view depicting angulation of the clamp and the screw.

By using spherical interfacing contact surfaces, a higher degree of angulation can be achieved. As shown in FIG. 35, the bone fastener 204 may be angled relative to the clamp member 207 and tulip element 210, respectively. In particular, the bone fastener 204 may be angled relative to a longitudinal axis of the tulip element 210. For example, up to ±41 degrees of angulation (82° total) may occur between the clamp element 207 and the bone fastener 204. In FIG. 35, there is no clamp angulation (i.e., zero degrees) such that a longitudinal axis of the clamp member 207 extends along the same longitudinal axis as the tulip element 210. A greater degree of angulation can be achieved by also angling the clamp member 207 relative to the tulip element 210. For example, up to ±9 degrees of angulation (18° total) may occur between the clamp element 207 and the tulip element 210. As shown in FIG. 36, the bone fastener 204 is angled relative to the clamp member 207 and the clamp member 207 is angled relative to the tulip element 210. Therefore, when combined, a total of up to ±50 degrees of angulation (100° total) in any direction may occur between the tulip element 210 and the bone fastener 204. This greater degree of conical angulation of the bone fastener 204 provides more versatility and options especially in rod constructions positioned in difficult or small spaces.

Once the tulip element 210 is at the desired position with respect to the bone fastener 204, the tulip element 210 may be locked onto the bone fastener 204. In the illustrated embodiment, the locking cap 212 is of a threaded type having an external threaded portion 290 extending from a first end to a second end of the locking cap 212. The locking cap 212 may also be provided with a recess, such as a hexalobular driving recess, for engagement with a driving instrument (not shown). The threaded locking cap 212 is configured to directly secure the rod 214 in the tulip element 210. Thus, the threaded locking cap 212, when secured to the tulip element 210, locks the screw 204 to the rod 214 and locks the bone fastener 204 into position, thereby fixing the degree of angulation of the bone fastener 204 relative to the tulip element 210.

Figure 37:
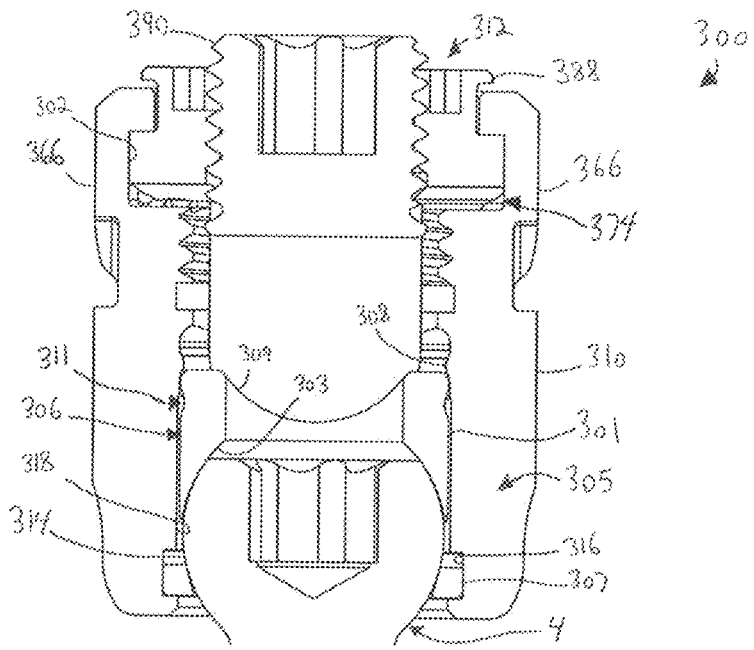
FIG. 37 illustrates a cross-sectional view of an orthopedic fixation device in accordance with embodiments of the present invention.

Referring now to FIG. 37, an orthopedic fixation device 300 is described in accordance with alternative embodiments of the present invention. The orthopedic fixation device 300 is substantially similar to the orthopedic fixation device 2 discussed above. As such, a description of similar elements and features will be omitted here for clarity. As illustrated, the orthopedic fixation device 300 comprises a bone fastener 4 (only the head 314 of the fastener is shown), a locking clamp assembly 305 having a saddle 306 and a retaining clip 307, a tulip element 310, and a locking cap assembly 312. In the illustrated embodiment, the saddle 306 includes a spherical lower surface 303 for receiving the head 314 of the bone fastener 4 and a curved upper surface 309 for receiving a rod (i.e., rod 14 discussed above). The saddle 306 is inserted into the tulip element 310 from the bottom until inwardly protruding shoulders 308 of an inner surface of the tulip element 310 engage corresponding engagement features 311, which are formed in an outer surface 301 of the saddle 306. As a result, the saddle 306 is locked in place during initial installation of the saddle 306 in the tulip element 310. Subsequently, the head 314 of the bone fastener 4 is inserted into the tulip element 310 from the bottom so that the head 314 is disposed beneath the saddle 306. To prevent the bone fastener 4 from falling out of the tulip element 310, the retaining clip 307 is inserted into an annular channel 316 formed in a distal portion of an inner wall 318 of the tulip element 310. Finally, the saddle 306 is pushed downward to overcome the engagement of the engagement features 311 with the shoulders 308 so that the saddle 306 limits axial movement of the bone fastener 4. As will be discussed below, an inner diameter of the retaining clip 307 is less than a maximum diameter of the head 314 of the bone fastener 4. As such, axial movement of the largest portion of the head 314 beyond the retaining clip 307 is prevented.

Figure 38A:
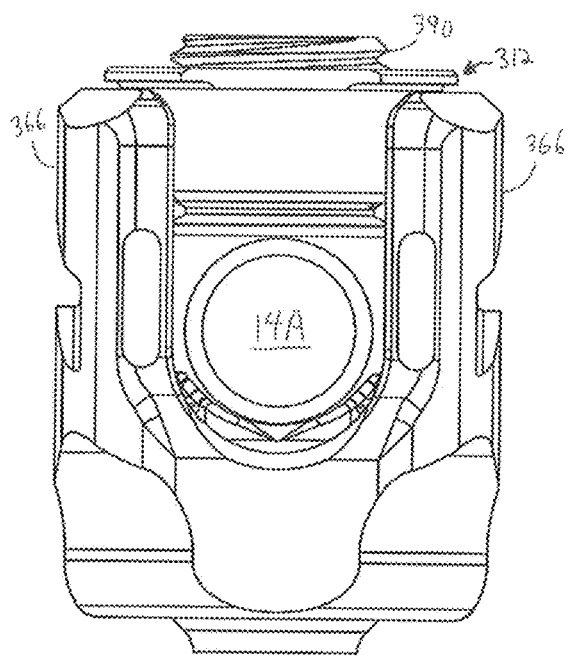
FIGS. 38A and 38B illustrate side views of an orthopedic fixation device in accordance with embodiments of the present invention.
Figure 38B:
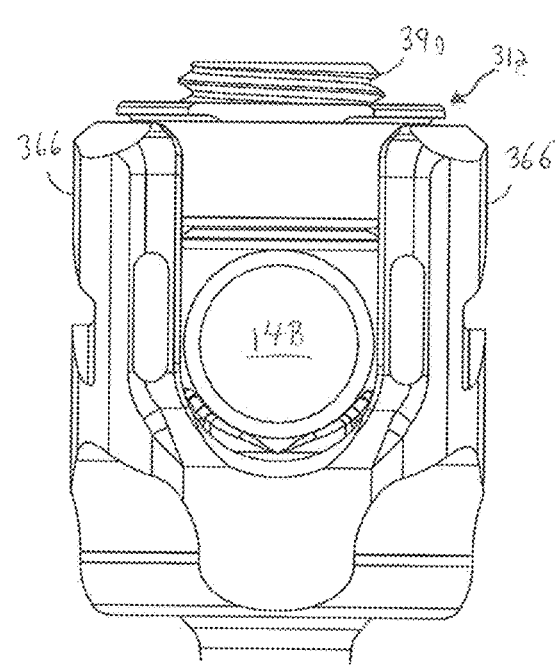

The orthopedic fixation device 300 may be configured to accommodate various-sized rods (e.g., rod 14). To provide such variability, the spacing between arms 366 of the tulip element 310 and a set screw 390 of the locking cap assembly 312 are configured to accommodate various-sized rods including, for example, rods having a diameter of about 5.5 mm and about 6.0 mm. FIG. 38A illustrates the fixation device 2 with a rod 14A having a first diameter (e.g., 5.5 mm). FIG. 38B illustrates the fixation device 2 with a rod 14B having a second diameter larger than the first diameter (e.g., 6.0 mm). The set screw 390 may be turned so that the male threads of the set screw 390 and the female threads in the body 388 of the locking cap assembly 312 engage to advance the set screw 390 further into the tulip element 310 until the set screw 390 contacts the rod 14A or 14B. Subsequently, the set screw 390 is advanced further downward to exert a downward force on the rod 14, which in turn exerts a downward force on the saddle 306 (not shown in FIGS. 38A, 38B) below the rod 14. As the set screw 390 is advanced further downward, the force exerted on the saddle 306 moves the saddle 306 downward, thus exerting a downward force on the head 314 of the bone fastener 4. The set screw 390 may be advanced far enough such that the head 314 is wedged between the saddle 306 and the retaining clip 307, as shown in FIG. 37.

Figure 39A:
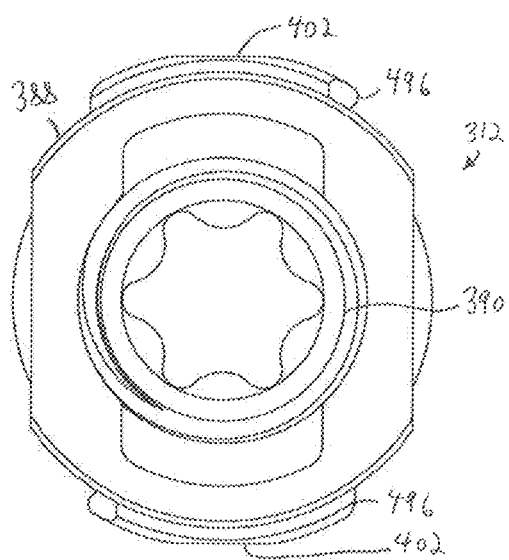
FIG. 39A illustrates a top view of a locking cap assembly in accordance with embodiments of the present invention.
Figure 39B:
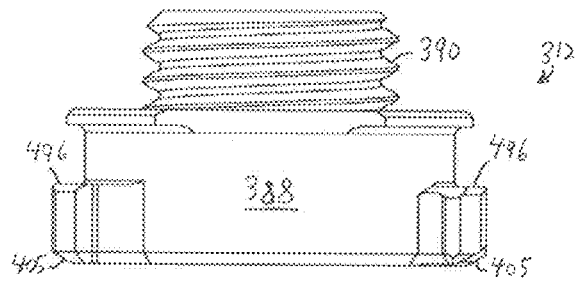
FIGS. 39B and 39C illustrate side views of a locking cap assembly in accordance with embodiments of the present invention.
Figure 39C:
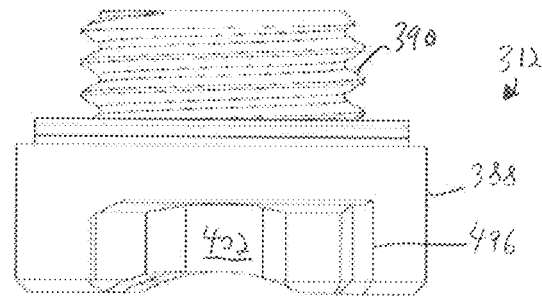

FIGS. 39A-39C illustrate the locking cap assembly 312 in accordance with embodiments of the present invention. The locking cap assembly 312 is similar to the locking cap assembly 12. As such, a description of similar elements or features will be omitted here for clarity. Similar to the locking cap assembly 12, the body 388 of the locking cap assembly 312 may include a pair of tabs 496 extending from opposite sides of the body 388. In some embodiments, a radially outermost surface of each tab 496 may include a flat portion 402, as shown more clearly in FIG. 39A. In such embodiments, a slot 374 (similar to the slot 74 discussed above) formed in the interior surface of the arms 366 of the tulip element 310 may include corresponding flat surfaces 302 (shown in FIG. 37). The flat portions 402 advantageously ensure correct positioning and locking in place of the body 388 when the locking cap assembly 312 is installed. As shown more clearly in FIG. 39B, in some embodiments, the tabs 496 may additionally include a positive lead angle 405 to advantageously reduce splay of the arms 366 during turning of the body 388 to lock the cap assembly 312 in the tulip element 310.

Figure 40A:
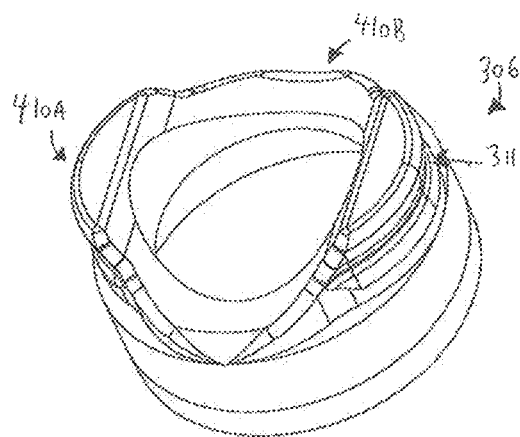
FIG. 40A illustrates an isometric view of a saddle in accordance with embodiments of the present invention.
Figure 40B:
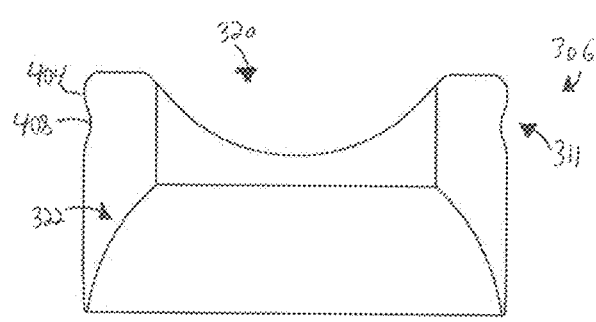
FIG. 40B illustrates a cross-sectional view of the saddle of FIG. 40A.

FIGS. 40A and 40B illustrate isometric and cross-sectional views, respectively, of the saddle 306 discussed above. As illustrated, the saddle 306 is similar to the wedge element 8 discussed above except that a bore 320 extending through the saddle 306 includes a lower portion 322 that is sized and shaped to receive at least a portion of the head 314 of the bone fastener 4 (as similarly depicted in the embodiments of FIG. 42). As noted above, in some embodiments, the outer surface 324 of the saddle 306 includes engagement features 311 disposed on opposite sides of the saddle 306 and configured to engage the inwardly protruding shoulders 308 of the tulip element 310 to lock the saddle 306 in place during initial installation of the saddle 306 in the tulip element 310. After insertion of the bone fastener 4 and the retaining clip 307 into the tulip element 310, the saddle 306 is pushed downward to overcome the engagement of the inwardly protruding shoulders 308 with the engagement features 311 to maintain appropriate clearance between the locking cap assembly 312 and the rod 14 when the locking cap assembly 312 is assembled during a surgical procedure. The engagement features 311 also serve to advantageously prevent upward axial motion of the saddle 306 after it has been moved into contact with the head 314.

In some embodiments, the engagement features 311 may include at least one protrusion 404 extending radially outward from the saddle 306 and at least one recess 408 adjacent the protrusion 404. The recess 408 is configured to receive the shoulder 308 of the tulip element 310. The protrusion 404 is configured to abut against the shoulder 308 after the saddle 306 has been pushed below the shoulder 308 to limit axial movement of the saddle 306 after the fastener 4 has been installed. In some embodiments, the saddle 306 may include at least two elliptical axial cross-sectional portions 410A and 410B to advantageously prevent rotation of the saddle 306 relative to and within the tulip element 310. In some embodiments, the first elliptical axial cross-sectional portion 410A extends perpendicularly to the second elliptical axial cross-sectional portion 410B, as illustrated in FIG. 40A. In some embodiments, a lower portion of the saddle 306 (e.g., the area of the saddle around the lower portion 322) may have an elliptical axial cross-section in the axial direction to advantageously provide additional support for the prevention of the rotation of the saddle 306 within the tulip element 310. In some embodiments, the lower portion of the saddle 306 may alternatively have a circular cross-section in the axial direction.

Figure 41:
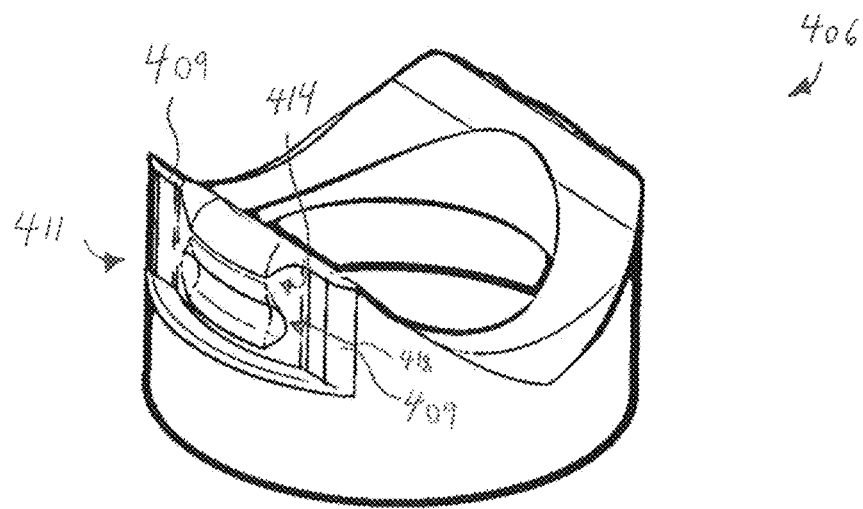
FIG. 41 illustrates an isometric view of a saddle in accordance with embodiments of the present invention.

FIG. 41 depicts a saddle 406 in accordance with alternative embodiments of the present invention. The saddle 406 is substantially similar to the saddle 306 described above. As such a description of similar elements and features will be omitted here for clarity. In some embodiments, the saddle 406 may include a pair of engagement features 411 (one visible in FIG. 41) disposed on opposite sides of the saddle 406. Similar to the engagement features 311, each engagement feature 411 includes at least one protrusion 414 and at least one recess 418. However, in the embodiment illustrated in FIG. 41, each engagement feature 411 may additionally include at least one flat surface 409 which interfaces with a corresponding flat surface (not shown) formed in the inner surface of the tulip element to advantageously prevent rotation of the saddle 406 within the tulip element.

Figure 42A:
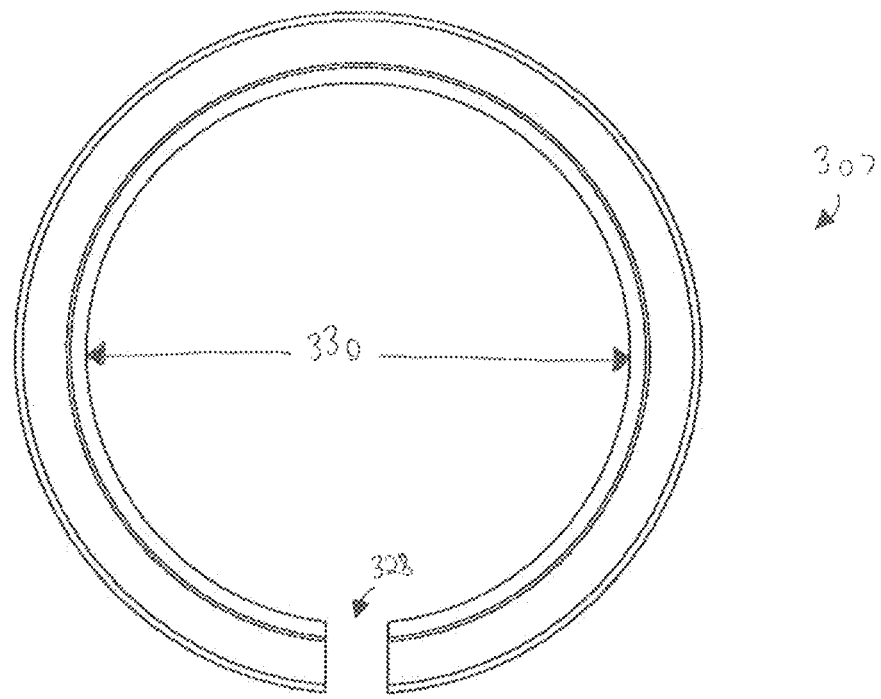
FIG. 42A illustrates a top view of a retaining clip in accordance with embodiments of the present invention.
Figure 42B:
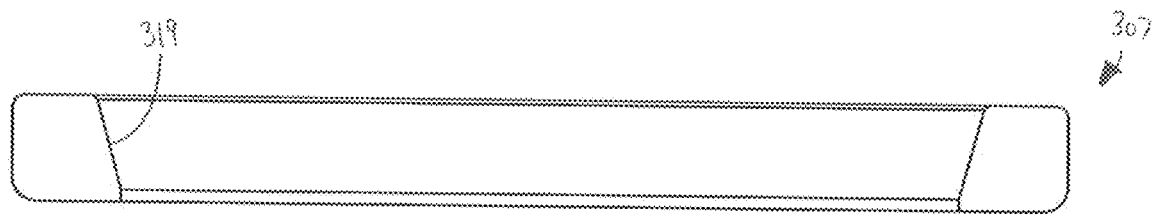
FIG. 42B illustrates a cross-sectional view of the retaining clip of FIG. 41A.

FIGS. 42A and 42B illustrate top and cross-sectional views, respectively, of the retaining clip 307 in accordance with embodiments of the present invention. In some embodiments, the retaining clip 307 is annular, as shown in FIG. 42A. It should be noted that the retaining clip 307 may have any suitable shape (e.g., elliptical, octagonal, etc.). As shown in FIG. 42A, the retaining clip 307 includes an opening 328 which extends through a thickness of the retaining clip 307. The opening 328 allows for the compression of the retaining clip 307 during installation of the retaining clip 307 in the annular channel 316 of the tulip element 310. To install the retaining clip 307 in the tulip element 310, the portions of the retaining clip 307 adjacent the opening 328 are pinched together, thereby reducing the effective diameter of the retaining clip 307, and subsequently placed in the annular channel 316. When the retaining clip 307 is released, it returns to its original size and can no longer be removed from the tulip element 310 without again pinching the clip again.

As noted above, an interior diameter 330 of the retaining clip 307 is smaller than the largest diameter of the head 314 of the bone fastener 4 to prevent the head 314 from moving beyond the retaining clip 307, thus retaining the bone fastener 4 in the tulip element 310. In some embodiments, an inner surface 319 of the retaining clip 307 may be angled to improve seating of the head 314 in the retaining clip 307 when the head 314 is wedged between the saddle 306 and the retaining clip 307. In some embodiments, the inner surface 319 may alternatively be arced or straight as long as the inner diameter of the retaining clip 307 is smaller than the largest diameter of the head 314. In some embodiments, the retaining clip 307 may be formed of any suitable material such as, for example, a titanium alloy, cobalt chromium, or stainless steel. However, it should be noted that the retaining clip 307 may alternatively be formed of any other suitable, biocompatible material.

Figure 43:
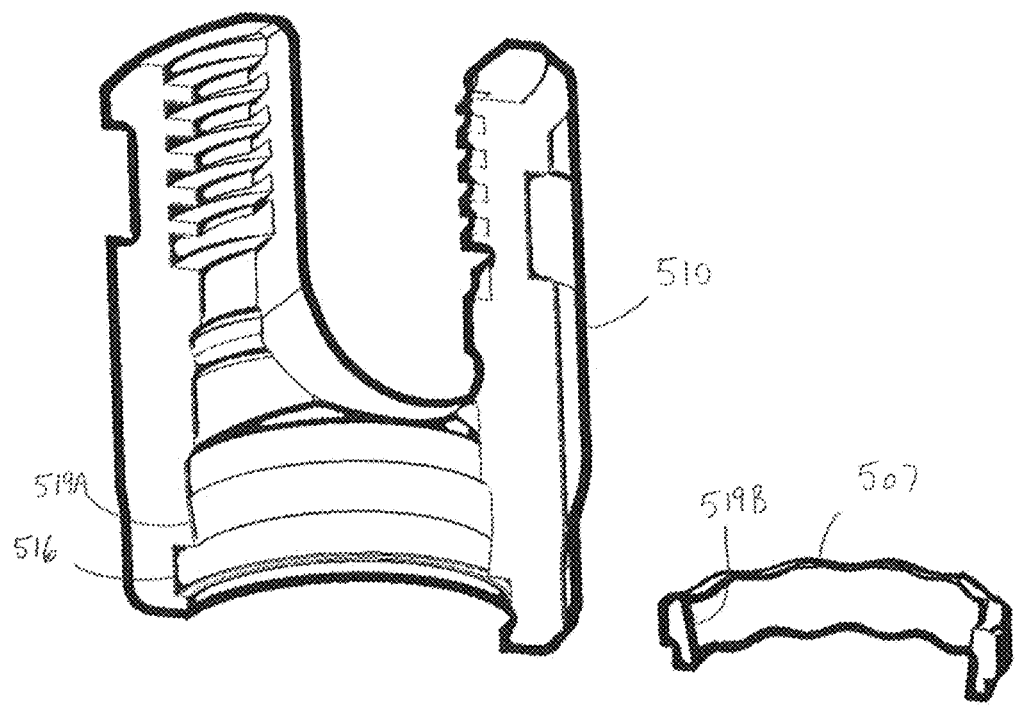
FIG. 43 illustrates an isometric cross-sectional view of a tulip element and retaining clip in accordance with embodiments of the present invention.

FIG. 43 illustrates a tulip element 510 and a retaining clip 507 of an orthopedic fixation device in accordance with embodiments of the present invention. The tulip element 510 is substantially similar to the tulip elements 10 and 310 discussed above. As such, a description of similar elements and features is omitted here for clarity. In the embodiment of FIG. 43, the tulip element 510 includes a first angled surface 519A disposed in a distal portion of the tulip element 510 above an annular channel 516 into which the retaining clip 507 is inserted. The retaining clip 507 includes a second angled surface 519B, which together with the first angled surface 519A, provides a locking taper to retain the head of a bone fastener (e.g., bone fastener 4, not shown in FIG. 43). In some embodiments, the tulip element 510 and the retaining clip 507 may be used in conjunction with a locking clamp assembly such as, for example, the locking clamp assembly 6. As the locking clamp assembly is pushed downward by the locking cap and rod, the clamp portions of the locking clamp assembly are forced radially inward, thus gripping the head of the bone fastener and locking the polyaxial motion of the bone fastener. In some embodiments, the upper and lower surfaces of the retaining clip 507 include a plurality of hills and valleys, as illustrated in FIG. 43, to advantageously lock the retaining clip 507 in place and prevent it from moving within the tulip element 510.

Figure 44:
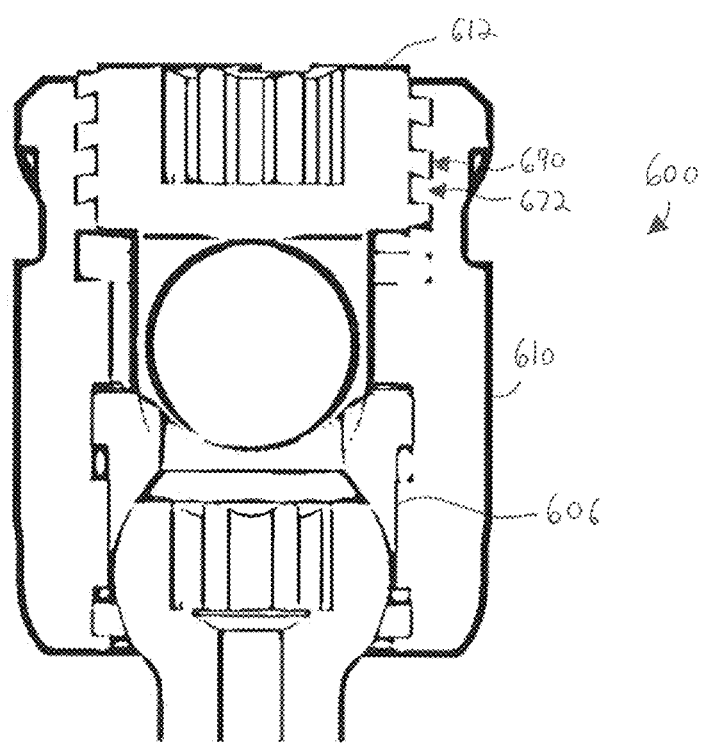
FIG. 44 illustrates an orthopedic fixation device in accordance with embodiments of the present invention.

FIG. 44 illustrates an orthopedic fixation device 600 in accordance with embodiments of the present invention. The orthopedic fixation device 600 is substantially similar to the orthopedic fixation device 300 discussed above, except that the orthopedic fixation device 600 includes (a) a tulip element 610 having an interior surface that is threaded and (b) a threaded locking cap 612. As illustrated in FIG. 44, the interior surface of the tulip element 610 may have a threaded portion 672 for engaging corresponding threads 690 of the threaded locking cap 612. Thus, the threaded locking cap 612 may be secured directly to the tulip element 610, for example, by rotating the threaded locking cap 612 into an upper portion of the tulip element 610, thus engaging the threads 672. As illustrated in FIG. 44, in some embodiments, the threaded engagement of the threaded locking cap 612 and the upper portion of the tulip element 610 may include a positive angle at the top angle of the threaded portion 672 and leading angles of the threads 690 (i.e., lower surfaces of the threads 690 of the threaded locking cap 612 and upper surfaces of threads of the threaded portion 672 of the coupling element 610 slope downward and outward). As a result, the threaded locking cap 612 is more securely held in place and splaying of the arms of the tulip element 610 is substantially reduced or eliminated. The orthopedic fixation device 600 also includes a saddle 606, which is substantially similar to the saddle 506 discussed above. However, in some embodiments, and as illustrated in FIG. 44, the flat portions and protrusions discussed above with respect to the saddle 306 may be omitted. In some embodiments, however, the saddle 606 may alternatively include such flat portions and protrusions. In addition, in some embodiments, the upper portion of the saddle 606 may have an elliptical cross-section when viewed in the axial direction. Similar to the saddle 506, the elliptical cross-section of the upper portion of the saddle 606 limits rotation of the saddle 606 within the tulip element. In the embodiment of FIG. 44, the saddle 606 may be inserted from the top of the tulip element and rotated into place. As a result, the more robust engagement of the saddle 606 with the tulip element is achieved, assembly is simplified, and a hard stop is provided to limit upward movement of the saddle 606.

Figure 45B:
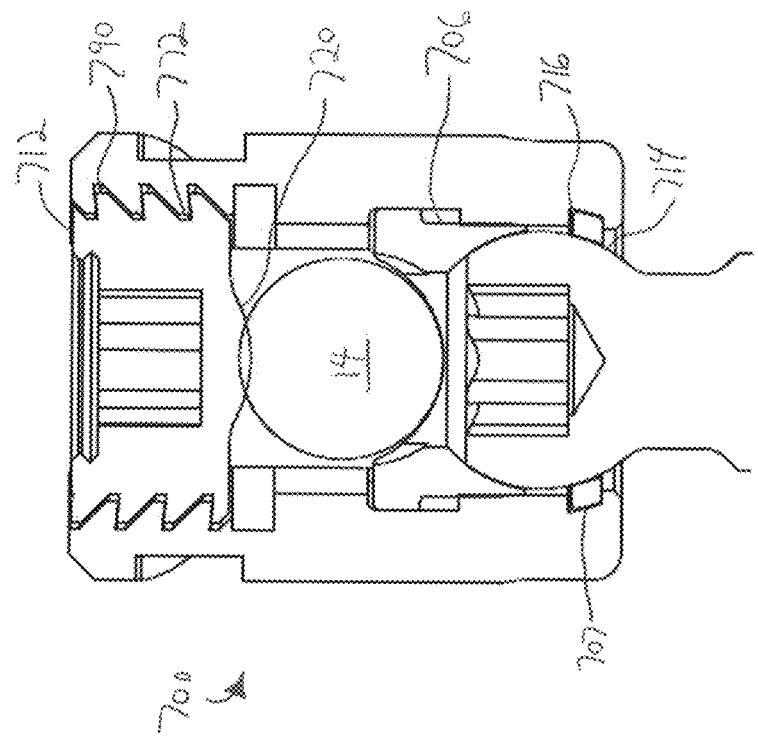
FIG. 45B illustrates a cross-sectional view of the orthopedic fixation device of FIG. 45A, as assembled.
Figure 45A:
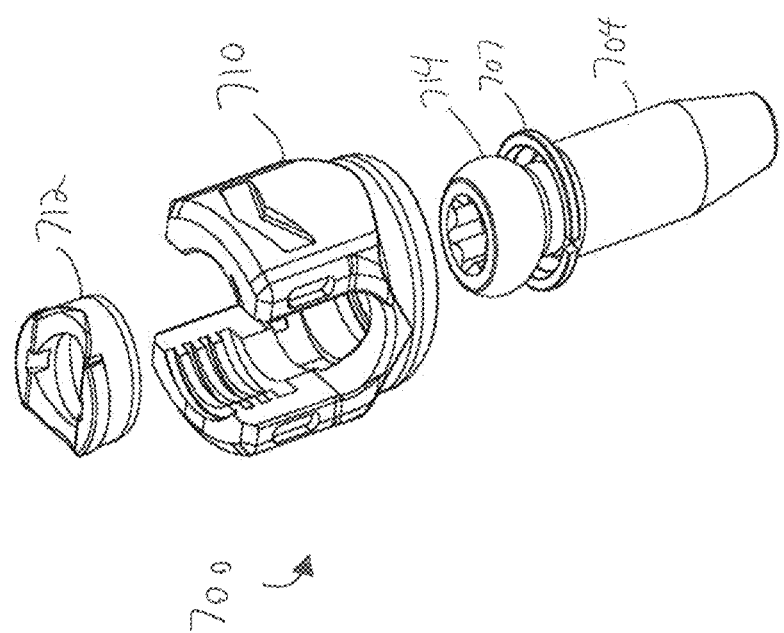
FIG. 45A illustrates an isometric exploded view of an orthopedic fixation device in accordance with embodiments of the present invention.

FIG. 45A depicts an isometric exploded view of an orthopedic fixation device 700 in accordance with embodiments of the present invention. FIG. 45B depicts a cross-sectional view of the orthopedic fixation device 700, as assembled. The orthopedic fixation device 700 is substantially similar to the orthopedic fixation device 300 discussed above. As such, a description of similar elements and features will be omitted here for clarity. The orthopedic fixation device 700 includes a locking cap 712, a tulip element 710, a bone fastener 704 having a head 714, a retaining clip 707, and a saddle 706. Similar to the orthopedic fixation device 300, the locking cap 712 is inserted into the tulip element 710 and rotated 90° to lock it into the tulip element 710. In some embodiments, the locking cap 712 may include a plurality of protrusions 790 which are disposed in a corresponding plurality of recesses 772 formed in an inner surface of the tulip element 790 to ensure that the locking cap 712 is securely locked in place. In some embodiments, the locking cap 712 may further include a downwardly protruding bump 720. The bump 720 advantageously allows for a downward force on a rod 14 and the saddle 706 without requiring the locking cap 712 to have threads. As a result, polyaxial motion of the bone fastener 704 can either be locked (when the locking cap 712 is rotated into position within the tulip element 710) or allowed (when the locking cap 712 is not rotated into position) without the necessity of repeatedly turning the locking cap 712 (as required when the locking cap includes threads).

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims. Although individual embodiments are discussed herein, the invention covers all combinations of all those embodiments.

What is claimed is:
1. An orthopedic fixation device comprising:
a coupling element having a bore extending therethrough, an interior surface disposed about the bore, and an annular channel formed in a distal portion of the interior surface;
a bone fastener, wherein the bone fastener comprises a head and an extension that extends from the head, wherein the head is configured for loading into the coupling element through the bottom of the bore;
a locking cap assembly, wherein the locking clamp assembly comprises:
a body having a bore extending through the body and a pair of tabs extending from opposite sides of the body, wherein the bore includes a threaded portion, and wherein a radially outermost surface of each tab includes a flat portion; and
a set screw extending through the bore of the body and having threads corresponding to the threaded portion of the bore of the body;
a saddle having a bore extending through the saddle, wherein the saddle includes a lower portion sized and shaped to receive at least a portion of the head of the bone fastener; and
a retaining clip disposed on an underside of the head of the fastener in the annular channel of the coupling element, wherein an inner diameter of the retaining clip is less than a maximum diameter of the head of the bone fastener, wherein an upper surface of the retaining clip has a plurality of peaks and troughs such that the peaks are adapted to lock the retaining clip to the fastener to prevent the fastener from moving relative to the coupling element;
wherein the retaining clip includes:
an upper annular portion having an upper inner surface and an outer surface that extends vertically downwardly and then laterally inwardly;
a lower annular portion having a lower inner surface and having an exterior surface that extends vertically downwardly from the laterally extending outer surface of the upper annular portion;
wherein the upper and lower inner surfaces of the retaining clip provide a continuous concave inner surface that contacts an outer surface of the fastener head.

2. The orthopedic fixation device of claim 1, wherein a lower portion of the saddle has an elliptical cross-section in the axial direction.

3. The orthopedic fixation device of claim 1, wherein the retaining clip is annular and includes an opening disposed through a thickness of the retaining clip.

4. The orthopedic fixation device of claim 3, wherein an inner surface of the retaining clip is angled.

5. The orthopedic fixation device of claim 1, wherein the saddle comprises engagement features disposed on opposite sides of an outer surface of the saddle and configured to engage inwardly protruding shoulders of the coupling element.

6. The orthopedic fixation device of claim 5, wherein the engagement features are protrusions.

7. The orthopedic fixation device of claim 1, wherein the saddle further comprises at least two elliptical axial cross-sectional portions configured to prevent the saddle from rotating relative to and within the coupling element.

8. The orthopedic fixation device of claim 1, wherein the saddle further comprises a first elliptical cross-sectional portion and a second elliptical cross-sectional portion extending perpendicular to the first elliptical cross-sectional portion.

9. The orthopedic fixation device of claim 1, wherein the coupling element is a tulip element having a plurality of arms configured to receive an elongate rod.

10. The orthopedic fixation device of claim 1, wherein a lower surface of the retaining clip also has a plurality of peaks and troughs.

11. The orthopedic fixation device of claim 10, wherein the plurality of peaks and troughs are arranged in an undulating manner.

12. An orthopedic fixation device comprising:
a tulip element, wherein the tulip element comprises a bore extending therethrough, an interior surface disposed about the bore, an annular channel formed in a distal portion of the interior surface, and a plurality of arms configured to receive an elongate rod;
a bone fastener, wherein the bone fastener comprises a head and an extension that extends from the head, wherein the head is configured for loading into the tulip element through the bottom of the bore;

a locking cap assembly, wherein the locking clamp assembly comprises:
- a body having a bore extending through the body and a pair of tabs extending from opposite sides of the body, wherein the bore includes a threaded portion, and wherein a radially outermost surface of each tab includes a flat portion; and
- a set screw extending through the bore of the body and having threads corresponding to the threaded portion of the bore of the body;

a saddle comprising:
- a bore extending through the saddle;
- a lower portion sized and shaped to receive at least a portion of the head of the bone fastener;
- engagement features disposed on opposite sides of an outer surface of the saddle and configured to engage inwardly protruding shoulders of the tulip element; and at least two elliptical cross-sectional portions; and
- a retaining clip disposed on an underside of the head of the fastener in the annular channel of the tulip element, wherein an inner diameter of the retaining clip is less than a maximum diameter of the head of the bone fastener, wherein an upper surface of the retaining clip has a plurality of peaks and troughs such that the peaks are adapted to lock the retaining clip to the fastener to prevent the fastener from moving relative to the coupling element;

wherein the retaining clip includes:
- an upper annular portion having an upper inner surface and an outer surface that extends vertically downwardly and then laterally inwardly;
- a lower annular portion having a lower inner surface and having an exterior surface that extends vertically downwardly from the laterally extending outer surface of the upper annular portion;
- wherein the upper and lower inner surfaces of the retaining clip provide a continuous concave inner surface that contacts an outer surface of the fastener head.

13. The orthopedic fixation device of claim 12, wherein a lower portion of the saddle has an elliptical cross-section in the axial direction.

14. The orthopedic fixation device of claim 12, wherein the retaining clip is annular and includes an opening disposed through a thickness of the retaining clip.

15. The orthopedic fixation device of claim 14, wherein an inner surface of the retaining clip is angled.

16. The orthopedic fixation device of claim 12, wherein a lower surface of the retaining clip also has a plurality of peaks and troughs.

17. An orthopedic fixation device comprising:
- a coupling element having a bore extending therethrough, an interior surface disposed about the bore, and an annular channel formed in a distal portion of the interior surface;
- a bone fastener, wherein the bone fastener comprises a head and an extension that extends from the head, wherein the head is configured for loading into the coupling element through the bottom of the bore;
- a threaded locking cap having threads that engage a corresponding threaded portion of the coupling element, wherein lower surfaces of the threads of the threaded locking cap and upper surfaces of threads of the threaded portion of the coupling element slope downward and outward;
- a saddle having a bore extending through the saddle, wherein the saddle includes a lower portion sized and shaped to receive at least a portion of the head of the bone fastener; and
- a retaining clip disposed on an underside of the head of the fastener in the annular channel of the coupling element, wherein an inner diameter of the retaining clip is less than a maximum diameter of the head of the bone fastener, wherein an upper surface of the retaining clip has a plurality of peaks and troughs such that the peaks are adapted to lock the retaining clip to the fastener to prevent the fastener from moving relative to the coupling element;

wherein the retaining clip includes:
- an upper annular portion having an upper inner surface and an outer surface that extends vertically downwardly and then laterally inwardly;
- a lower annular portion having a lower inner surface and having an exterior surface that extends vertically downwardly from the laterally extending outer surface of the upper annular portion;
- wherein the upper and lower inner surfaces of the retaining clip provide a continuous concave inner surface that contacts an outer surface of the fastener head.

18. The orthopedic fixation device of claim 17, wherein a lower surface of the retaining clip also has a plurality of peaks and troughs.

* * * * *